United States Patent [19]
Livant

[11] Patent Number: 6,140,068
[45] Date of Patent: Oct. 31, 2000

[54] PROTEASE RESISTANT COMPOSITIONS FOR WOUND HEALING

[75] Inventor: Donna L. Livant, Ann Arbor, Mich.

[73] Assignee: The Regents of the University of Michigan, Ann Arbor, Mich.

[21] Appl. No.: 09/089,645

[22] Filed: Jun. 3, 1998

Related U.S. Application Data

[63] Continuation of application No. 08/972,760, Nov. 18, 1997, which is a continuation-in-part of application No. 08/754,322, Nov. 21, 1996.

[51] Int. Cl.$^7$ .............................. C12Q 1/02; C12Q 1/37; C12Q 1/00
[52] U.S. Cl. .............................. 435/29; 435/23; 435/24; 435/4; 530/300; 530/330; 530/350
[58] Field of Search .................................. 435/29, 23, 24, 435/4; 530/300, 330, 350

[56] References Cited

U.S. PATENT DOCUMENTS

| | | | |
|---|---|---|---|
| 5,051,448 | 9/1991 | Shashoua | 514/547 |
| 5,136,023 | 8/1992 | Hashino et al. | 435/29 |
| 5,169,862 | 12/1992 | Burke, Jr. et al. | 514/450 |
| 5,192,746 | 3/1993 | Lobl et al. | 514/11 |
| 5,492,890 | 2/1996 | Ginsburg et al. | 514/12 |
| 5,539,085 | 7/1996 | Bischoff et al. | 530/350 |
| 5,559,103 | 9/1996 | Gaeta et al. | 514/54 |
| 5,576,423 | 11/1996 | Aversa et al. | 530/388.75 |

OTHER PUBLICATIONS

Hunt and Goodson, "Current Surgical Diagnosis & Treatment" (Way; Appleton & Lange), pp. 86–98 (1988).
M. Harris et al., "Prevalence of Diabetes and Impaired Glucose Tolerance and Glucose Levels in the US Population aged 20–74 Years," *Diabetes*, 36:523 (1987).
Winter, "Formation of the Scab and the Rate of Epithelization of Superficial Wounds in the skin of the Young Domestic Pig," *Nature*, 193:293–94 (1962).
Kannon and Garret, "Moist Wound Healing with Occlusive Dressings," *Dermatol. Surg.*, 21:583–590 (1995).
Davies, "Synthetic Material for covering burn wounds: Progress towards perfection. Part 1. Short term dressing materials," *Burns*, 10:94 (1983).
Riley, "Wound Healing," *Am. Fam. Physician*, 24:107 (1981).
D. Livant et al., "Invasion of Selectively Sea Urchin Embryo Basement Membranes by Metastic Tumor Cells, But Not By Their Normal Counterparts," *Cancer Research*, 55:5085 (1995).
Eldred et al., "Orally Active Non–Peptide Fibrinogen (GpIIb/IIIa) Antagonists: Identification of 4–[4–[4–(Aminoiminomethyl) phenyl]–1–piperazinyl]–1–piperidineactic Acid as a Long–Acting, Broad Spectrum Antithrombotic Agent," *J. Med. Chem.*, 37:3882 (1994).
Ku et al., "Potent Non–Peptide Fibrinogen Receptor Antagonists Which Present An Alternative Pharmacophore," *J. Med. Chem.*, 38:9 (1995).
W.R. Pearson and D.J. Lipman, "Improved Tools for Biological Sequence Comparison," *Proc. Natl. Acad. Sci. (USA)*, 85:2444–2448 (1988).
D.J. Lipman and W.R. Pearson, "Rapid and Sensitive Protein Similarity Searches," *Science*, 227:1435–1441 (1985).
D.F. Mosher, "Physiology of Fibronectin," *Ann. Rev. Med.*, 35:561 (1984).
P. Huhtala et al., "Cooperative Signaling by $\alpha 5\beta 1$ and $\alpha 4\beta 1$ Integrins Regulates Metalloproteinase Gene Expression in Fibroblasts Adhering to Fibronectin," *J. Cell. Biol.*, 129:867 (1995).

(List continued on next page.)

*Primary Examiner*—Louise N. Leary
*Attorney, Agent, or Firm*—Medlen & Carroll, LLP

[57] ABSTRACT

Assays employing fibronectin-depleted substrates are described to identify invasion inducing agents. Such agents are useful for in vivo wound healing, including but not limited to deep wounds and chronic wounds.

18 Claims, 10 Drawing Sheets

OTHER PUBLICATIONS

Greiling and Clark, "Fibronectin provides a conduit for fibroblasts transmigration from collagenous stroma into fibrin clot provisional matrix," *J. of Cell Science,* 110:861–870 (1997).

Clark et al., "Cryptic Chemotactic Activity of Fibronectin for Human Monocytes Resides in the 120 kDa Fibroblastic Cell–binding Fragment," *J. Biol. Chem.,* 263: 12115–12123 (1988).

Clark et al., "Fibronectin and Fibrin Provide a Provisional Matrix for Epidermal Cell Migration During Wound Reepithelialization," *J of Invest. Dermatol.,* 79:264–269 (1982).

Clark, "Fibronectin Matrix Deposition and Fibronectin Receptor Expression in Healing and Normal Skin," *J. of Invest. Dermatol.,* 94(6): 128S–134S (1990).

Aota, S. et al., "The Short Amino Acid Sequence Pro–His–Ser–Arg–Asn in Human Fibronectin Cell–Adhesive Function," *J. Biol. Chem.,* 269(40): 24756–24761 (1994).

Aota, S. et al., "Characterization of Regions of Fibronectin Besides the Arginine–Glycine–Aspartic Acid Sequence Required for Adhesive Function of the Cell–binding Domain Using Site–directed Mutagensis," *J. Biol. Chem.,* 266(24): 15938–15943 (1991).

O'Donnell et al., "Structure–Activity Studies of Vasoactive Intestinal Polypeptide," *J. of Biol. Chemistry,* vol. 266, 10:6389–6392 (1991).

SEQUENCE LISTING

```
(1) GENERAL INFORMATION:

(iii) NUMBER OF SEQUENCES: 86

(2) INFORMATION FOR SEQ ID NO:1:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:1:

Pro His Ser Arg Asn
1               5

(2) INFORMATION FOR SEQ ID NO:2:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:2:

Ile Lys Val Ala Val
1               5

(2) INFORMATION FOR SEQ ID NO:3:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:3:

Pro His Ser Arg Asn Ser
1               5
```

```
(2) INFORMATION FOR SEQ ID NO:4:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:4:

Pro His Ser Arg Asn Ser Ile
1               5

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:5:

Pro His Ser Arg Asn Ser Ile Thr
1               5

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:6:

Pro His Ser Arg Asn Ser Ile Thr Leu
1               5

(2) INFORMATION FOR SEQ ID NO:7:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:7:

Pro His Ser Arg Asn Ser Ile Thr Leu Thr
1               5                   10

(2) INFORMATION FOR SEQ ID NO:8:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:8:

Pro His Ser Arg Asn Ser Ile Thr Leu Thr Asn
1               5                   10
```

(2) INFORMATION FOR SEQ ID NO:9:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:9:

Pro His Ser Arg Asn Ser Ile Thr Leu Thr Asn Leu
1               5                   10

(2) INFORMATION FOR SEQ ID NO:10:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:10:

Pro His Ser Arg Asn Ser Ile Thr Leu Thr Asn Leu Thr
1               5                   10

(2) INFORMATION FOR SEQ ID NO:11:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:11:

Pro His Ser Arg Asn Ser Ile Thr Leu Thr Asn Leu Thr Pro
1               5                   10

(2) INFORMATION FOR SEQ ID NO:12:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:12:

Pro His Ser Arg Asn Ser Ile Thr Leu Thr Asn Leu Thr Pro Gly
1               5                   10                  15

(2) INFORMATION FOR SEQ ID NO:13:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:13:

Pro Glu His Phe Ser Gly Arg Pro Arg Glu Asp Arg Val Pro His Ser
1               5                   10                  15

Arg Asn (2) INFORMATION FOR SEQ ID NO:14:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:14:

Glu His Phe Ser Gly Arg Pro Arg Glu Asp Arg Val Pro His Ser Arg
1               5                   10              15

Asn (2) INFORMATION FOR SEQ ID NO:15:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:15:

His Phe Ser Gly Arg Pro Arg Glu Asp Arg Val Pro His Ser Arg Asn
1               5                   10              15

(2) INFORMATION FOR SEQ ID NO:16:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:16:

Phe Ser Gly Arg Pro Arg Glu Asp Arg Val Pro His Ser Arg Asn
1               5                   10              15

(2) INFORMATION FOR SEQ ID NO:17:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:17:

Ser Gly Arg Pro Arg Glu Asp Arg Val Pro His Ser Arg Asn
1               5                   10

(2) INFORMATION FOR SEQ ID NO:18:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:18:

Gly Arg Pro Arg Glu Asp Arg Val Pro His Ser Arg Asn
1               5                   10

(2) INFORMATION FOR SEQ ID NO:19:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:19:

Arg Pro Arg Glu Asp Arg Val Pro His Ser Arg Asn
1               5                   10

(2) INFORMATION FOR SEQ ID NO:20:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:20:

Pro Arg Glu Asp Arg Val Pro His Ser Arg Asn
1               5                   10

(2) INFORMATION FOR SEQ ID NO:21:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:21:

Arg Glu Asp Arg Val Pro His Ser Arg Asn
1               5                   10

(2) INFORMATION FOR SEQ ID NO:22:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:22:

Glu Asp Arg Val Pro His Ser Arg Asn
1               5

(2) INFORMATION FOR SEQ ID NO:23:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:23:

Asp Arg Val Pro His Ser Arg Asn
1               5

(2) INFORMATION FOR SEQ ID NO:24:

(i) SEQUENCE CHARACTERISTICS:
         (A) LENGTH: 7 amino acids
         (B) TYPE: amino acid
         (C) STRANDEDNESS: Not Relevant
         (D) TOPOLOGY: Not Relevant (ii) MOLECULE TYPE: peptide (xi) SEQUENCE DESCRIPTION: SEQ ID NO:24:

Arg Val Pro His Ser Arg Asn
1               5

(2) INFORMATION FOR SEQ ID NO:25:

(i) SEQUENCE CHARACTERISTICS:
         (A) LENGTH: 6 amino acids
         (B) TYPE: amino acid
         (C) STRANDEDNESS: Not Relevant
         (D) TOPOLOGY: Not Relevant (ii) MOLECULE TYPE: peptide (xi) SEQUENCE DESCRIPTION: SEQ ID NO:25:

Val Pro His Ser Arg Asn
1               5

(2) INFORMATION FOR SEQ ID NO:26:

(i) SEQUENCE CHARACTERISTICS:
         (A) LENGTH: 28 amino acids
         (B) TYPE: amino acid
         (C) STRANDEDNESS: Not Relevant
         (D) TOPOLOGY: Not Relevant (ii) MOLECULE TYPE: peptide (xi) SEQUENCE DESCRIPTION: SEQ ID NO:26:

Pro Glu His Phe Ser Gly Arg Pro Arg Glu Asp Arg Val Pro His Ser
1               5                   10                  15

Arg Asn Ser Ile Thr Leu Thr Asn Leu Thr Pro Gly
            20                  25

(2) INFORMATION FOR SEQ ID NO:27:

(i) SEQUENCE CHARACTERISTICS:
         (A) LENGTH: 5 amino acids
         (B) TYPE: amino acid
         (C) STRANDEDNESS: Not Relevant
         (D) TOPOLOGY: Not Relevant (ii) MOLECULE TYPE: peptide (xi) SEQUENCE DESCRIPTION: SEQ ID NO:27:

Pro Pro Ser Arg Asn
1               5

(2) INFORMATION FOR SEQ ID NO:28:

(i) SEQUENCE CHARACTERISTICS:
         (A) LENGTH: 5 amino acids (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:28:

His His Ser Arg Asn
1               5

(2) INFORMATION FOR SEQ ID NO:29:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:29:

His Pro Ser Arg Asn
1               5

(2) INFORMATION FOR SEQ ID NO:30:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:30:

Pro His Thr Arg Asn
1               5

(2) INFORMATION FOR SEQ ID NO:31:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:31:

His His Thr Arg Asn
1               5

(2) INFORMATION FOR SEQ ID NO:32:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:32:

His Pro Thr Arg Asn
1               5

(2) INFORMATION FOR SEQ ID NO:33:

(i) SEQUENCE CHARACTERISTICS:

(A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:33:

Pro His Ser Asn Asn
1               5

(2) INFORMATION FOR SEQ ID NO:34:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:34:

His His Ser Asn Asn
1               5

(2) INFORMATION FOR SEQ ID NO:35:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:35:

His Pro Ser Asn Asn
1               5

(2) INFORMATION FOR SEQ ID NO:36:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:36:

Pro His Thr Asn Asn
1               5

(2) INFORMATION FOR SEQ ID NO:37:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:37:

His His Thr Asn Asn
1               5

(2) INFORMATION FOR SEQ ID NO:38:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:38:

His Pro Thr Asn Asn
1               5

(2) INFORMATION FOR SEQ ID NO:39:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:39:

Pro His Ser Lys Asn
1               5

(2) INFORMATION FOR SEQ ID NO:40:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:40:

His His Ser Lys Asn
1               5

(2) INFORMATION FOR SEQ ID NO:41:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:41:

His Pro Ser Lys Asn
1               5

(2) INFORMATION FOR SEQ ID NO:42:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:42:

Pro His Thr Lys Asn
1               5

(2) INFORMATION FOR SEQ ID NO:43:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:43:

His His Thr Lys Asn
1               5

(2) INFORMATION FOR SEQ ID NO:44:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:44:

His Pro Thr Lys Asn
1               5

(2) INFORMATION FOR SEQ ID NO:45:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:45:

Pro His Ser Arg Arg
1               5

(2) INFORMATION FOR SEQ ID NO:46:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:46:

His His Ser Arg Arg
1               5

(2) INFORMATION FOR SEQ ID NO:47:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:47:

His Pro Ser Arg Arg
1               5

```
(2) INFORMATION FOR SEQ ID NO:48:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:48:

Pro His Thr Arg Arg
1               5

(2) INFORMATION FOR SEQ ID NO:49:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:49:

His His Thr Arg Arg
1               5

(2) INFORMATION FOR SEQ ID NO:50:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:50:

His Pro Thr Arg Arg
1               5

(2) INFORMATION FOR SEQ ID NO:51:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:51:

Pro His Ser Asn Arg
1               5

(2) INFORMATION FOR SEQ ID NO:52:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:52:

His His Ser Asn Arg
1               5
```

(2) INFORMATION FOR SEQ ID NO:53:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:53:

His Pro Ser Asn Arg
1               5

(2) INFORMATION FOR SEQ ID NO:54:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:54:

Pro His Thr Asn Arg
1               5

(2) INFORMATION FOR SEQ ID NO:55:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:55:

His His Thr Asn Arg
1               5

(2) INFORMATION FOR SEQ ID NO:56:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:56:

His Pro Thr Asn Arg
1               5

(2) INFORMATION FOR SEQ ID NO:57:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:57:

Pro His Ser Lys Arg
1               5

(2) INFORMATION FOR SEQ ID NO:58:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:58:

His His Ser Lys Arg
1               5

(2) INFORMATION FOR SEQ ID NO:59:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:59:

His Pro Ser Lys Arg
1               5

(2) INFORMATION FOR SEQ ID NO:60:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:60:

Pro His Thr Lys Arg
1               5

(2) INFORMATION FOR SEQ ID NO:61:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:61:

His His Thr Lys Arg
1               5

(2) INFORMATION FOR SEQ ID NO:62:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:62:

His Pro Thr Lys Arg

```
1               5

(2) INFORMATION FOR SEQ ID NO:63:

(i) SEQUENCE CHARACTERISTICS:
         (A) LENGTH: 5 amino acids
         (B) TYPE: amino acid
         (C) STRANDEDNESS: Not Relevant
         (D) TOPOLOGY: Not Relevant (ii) MOLECULE TYPE: peptide (xi) SEQUENCE DESCRIPTION: SEQ ID NO:63:

Pro His Ser Arg Lys
1               5

(2) INFORMATION FOR SEQ ID NO:64:

(i) SEQUENCE CHARACTERISTICS:
         (A) LENGTH: 5 amino acids
         (B) TYPE: amino acid
         (C) STRANDEDNESS: Not Relevant
         (D) TOPOLOGY: Not Relevant (ii) MOLECULE TYPE: peptide (xi) SEQUENCE DESCRIPTION: SEQ ID NO:64:

His His Ser Arg Lys
1               5

(2) INFORMATION FOR SEQ ID NO:65:

(i) SEQUENCE CHARACTERISTICS:
         (A) LENGTH: 5 amino acids
         (B) TYPE: amino acid
         (C) STRANDEDNESS: Not Relevant
         (D) TOPOLOGY: Not Relevant (ii) MOLECULE TYPE: peptide (xi) SEQUENCE DESCRIPTION: SEQ ID NO:65:

His Pro Ser Arg Lys
1               5

(2) INFORMATION FOR SEQ ID NO:66:

(i) SEQUENCE CHARACTERISTICS:
         (A) LENGTH: 5 amino acids
         (B) TYPE: amino acid
         (C) STRANDEDNESS: Not Relevant
         (D) TOPOLOGY: Not Relevant (ii) MOLECULE TYPE: peptide (xi) SEQUENCE DESCRIPTION: SEQ ID NO:66:

Pro His Thr Arg Lys
1               5

(2) INFORMATION FOR SEQ ID NO:67:

(i) SEQUENCE CHARACTERISTICS:
         (A) LENGTH: 5 amino acids
         (B) TYPE: amino acid
         (C) STRANDEDNESS: Not Relevant
         (D) TOPOLOGY: Not Relevant (ii) MOLECULE TYPE: peptide (xi) SEQUENCE DESCRIPTION: SEQ ID NO:67:
```

```
His His Thr Arg Lys
1               5

(2) INFORMATION FOR SEQ ID NO:68:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:68:

His Pro Thr Arg Lys
1               5

(2) INFORMATION FOR SEQ ID NO:69:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:69:

Pro His Ser Asn Lys
1               5

(2) INFORMATION FOR SEQ ID NO:70:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:70:

His His Ser Asn Lys
1               5

(2) INFORMATION FOR SEQ ID NO:71:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:71:

His Pro Ser Asn Lys
1               5

(2) INFORMATION FOR SEQ ID NO:72:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:72:
```

Pro His Thr Asn Lys
1               5

(2) INFORMATION FOR SEQ ID NO:73:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:73:

His His Thr Asn Lys
1               5

(2) INFORMATION FOR SEQ ID NO:74:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:74:

His Pro Thr Asn Lys
1               5

(2) INFORMATION FOR SEQ ID NO:75:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:75:

Pro His Ser Lys Lys
1               5

(2) INFORMATION FOR SEQ ID NO:76:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:76:

His His Ser Lys Lys
1               5

(2) INFORMATION FOR SEQ ID NO:77:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:77:

His Pro Ser Lys Lys
1               5

(2) INFORMATION FOR SEQ ID NO:78:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:78:

Pro His Thr Lys Lys
1               5

(2) INFORMATION FOR SEQ ID NO:79:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:79:

His His Thr Lys Lys
1               5

(2) INFORMATION FOR SEQ ID NO:80:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:80:

His Pro Thr Lys Lys
1               5

(2) INFORMATION FOR SEQ ID NO:81:

(i) SEQUENCE CHARACTERISTICS:
            (A) LENGTH: 3 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:81:

Arg Gly Asp
1

(2) INFORMATION FOR SEQ ID NO:82:

(i) SEQUENCE CHARACTERISTICS:
            (A) LENGTH: 6 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:82:

Pro His Ser Arg Asn Cys
1               5

(2) INFORMATION FOR SEQ ID NO:83:

(i) SEQUENCE CHARACTERISTICS:
          (A) LENGTH: 5 amino acids
          (B) TYPE: amino acid
          (C) STRANDEDNESS: Not Relevant
          (D) TOPOLOGY: Not Relevant (ii) MOLECULE TYPE: peptide (xi) SEQUENCE DESCRIPTION: SEQ ID NO:83:

Gly Arg Gly Asp Ser
1               5

(2) INFORMATION FOR SEQ ID NO:84:

(i) SEQUENCE CHARACTERISTICS:
          (A) LENGTH: 9 amino acids
          (B) TYPE: amino acid
          (C) STRANDEDNESS: Not Relevant
          (D) TOPOLOGY: Not Relevant (ii) MOLECULE TYPE: peptide (ix) FEATURE:
          (A) NAME/KEY: Modified-site
          (B) LOCATION: 1
          (D) OTHER INFORMATION: /note= "This X is a placeholder for
               N-terminal acetylation."

(ix) FEATURE:
          (A) NAME/KEY: Modified-site
          (B) LOCATION: 9
          (D) OTHER INFORMATION: /note= "X represents an amino
               group."

(ix) FEATURE:
          (A) NAME/KEY: Modified-site
          (B) LOCATION: 2
          (D) OTHER INFORMATION: /note= "The number of amino acids
               at this position may vary from between 0 and 100, or
               more."

(ix) FEATURE:
          (A) NAME/KEY: Modified-site
          (B) LOCATION: 8
          (D) OTHER INFORMATION: /note= "The number of amino acids
               at this position may vary from between 0 and 100, or
               more."

(xi) SEQUENCE DESCRIPTION: SEQ ID NO:84:

Xaa Xaa Pro His Ser Arg Asn Xaa Xaa
1               5

(2) INFORMATION FOR SEQ ID NO:85:

(i) SEQUENCE CHARACTERISTICS:
          (A) LENGTH: 5 amino acids
          (B) TYPE: amino acid
          (C) STRANDEDNESS: Not Relevant
          (D) TOPOLOGY: Not Relevant (ii) MOLECULE TYPE: peptide (xi) SEQUENCE DESCRIPTION: SEQ ID NO:85:

Pro Pro Ser Arg Asn
1               5

```
(2) INFORMATION FOR SEQ ID NO:86:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Modified-site
        (B) LOCATION: 4
        (D) OTHER INFORMATION: /note= "The residue in this
             position can be either Arg or Asp"

(xi) SEQUENCE DESCRIPTION: SEQ ID NO:86:

Pro His Ser Arg Asn
1               5
```

PROTEASE RESISTANT COMPOSITIONS FOR WOUND HEALING

This application is a continuation of U.S. application Ser. No. 08/972,760 filed Nov. 18, 1997, which is a continuation-in-part of U.S. application Ser. No. 08/754,322 filed on Nov. 21, 1996.

FIELD OF THE INVENTION

The present invention relates to methods and compositions for wound healing, and in particular, methods and compositions to promote and enhance wound healing.

BACKGROUND

The primary goal in the treatment of wounds is to achieve wound closure. Open cutaneous wounds represent one major category of wounds and include burn wounds, neuropathic ulcers, pressure sores, venous stasis ulcers, and diabetic ulcers. Open cutaneous wounds routinely heal by a process which comprises six major components: i) inflammation, ii) fibroblast proliferation, iii) blood vessel proliferation, iv) connective tissue synthesis v) epithelialization, and vi) wound contraction. Wound healing is impaired when these components, either individually or as a whole, do not function properly. Numerous factors can affect wound healing, including malnutrition, infection, pharmacological agents (e.g., actinomycin and steroids), diabetes, and advanced age [see Hunt and Goodson in *Current Surgical Diagnosis & Treatment* (Way; Appleton & Lange), pp. 86–98 (1988)].

With respect to diabetes, it is known that delayed wound healing causes substantial morbidity in patients with diabetes. Diabetes mellitus is a chronic disorder of glucose metabolism and homeostasis that damages many organs. It is the eighth leading cause of death in the United States. M. Harris et al., "Prevalence of Diabetes and Impaired Glucose Tolerance and Glucose Levels in the US Population aged 20–40 Years," *Diabetes* 36:523 (1987). In persons with diabetes, vascular disease, neuropathy, infections, and recurrent trauma predispose the extremities, especially the foot, to pathologic changes. These pathological changes can ultimately lead to chronic ulceration, which may necessitate amputation.

The most commonly used conventional modality to assist in wound healing involves the use of wound dressings. In the 1960s, a major breakthrough in wound care occurred when it was discovered that wound healing with a moist occlusive dressings was, generally speaking, more effective than the use of dry, non-occlusive dressings [Winter, Nature 193:293–94 (1962)]. Today, numerous types of dressings are routinely used, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), and cellophane (cellulose with a plasticizer) [Kannon and Garrett, Dermatol. Surg. 21:583–590 (1995); Davies, *Burns* 10:94 (1983)]. Unfortunately, certain types of wounds (e.g., diabetic ulcers, pressure sores) and the wounds of certain subjects (e.g., recipients of exogenous corticosteroids) do not heal in a timely manner (or at all) with the use of such dressings.

Several pharmaceutical modalities have also been utilized in an attempt to improve wound healing. For example, treatment regimens involving zinc sulfate have been utilized by some practitioners. However, the efficacy of these regimens has been primarily attributed to their reversal of the effects of sub-normal serum zinc levels (e.g., decreased host resistance and altered intracellular bactericidal activity) [Riley, *Am. Fam. Physician* 24:107 (1981)]. While other vitamin and mineral deficiencies have also been associated with decreased wound healing (e.g., deficiencies of vitamins A, C and D; and calcium, magnesium, copper, and iron), there is no strong evidence that increasing the serum levels of these substances above their normal levels actually enhances wound healing. Thus, except in very limited circumstances, the promotion of wound healing with these agents has met with little success.

What is needed is a safe, effective, and interactive means for enhancing the healing of wounds. The means should be able to be used without regard to the type of wound or the nature of the patient population to which the subject belongs.

SUMMARY OF THE INVENTION

The present invention is directed at systems and methods for enhancing the healing of wounds, especially chronic wounds (e.g., diabetic wounds, pressure sores). The compositions of the present invention are based on the discovery that peptides containing the amino acid sequence PHSRN (SEQ ID NO:1) promote wound healing. The present invention contemplates the use of such peptides, peptide derivatives, protease-resistant peptides, and non-peptide mimetics in the treatment of wounds.

It is not intended that the present invention be limited to the mode by which the compositions of the present invention are introduced to the patient. In one embodiment, the present invention contemplates systemic administration of the compound (e.g. intravenous). In another embodiment, the present invention contemplates topical administration, including but not limited to topical administration using solid supports (such as dressings and other matrices) and medicinal formulations (such as mixtures, suspensions and ointments). In one embodiment, the solid support comprises a biocompatible membrane. In another embodiment, the solid support comprises a wound dressing. In still another embodiment, the solid support comprises a band-aid.

The present invention contemplates a method for treating a wound, comprising a) providing: i) an invasion-inducing agent, and ii) a subject having at least one wound; and b) administering said invasion-inducing agent to said subject under conditions such that the healing of said wound is promoted.

The present invention also contemplates a method for treating a wound, comprising a) providing: i) an invasion-inducing agent on a solid support, and ii) a subject having at least one wound; and b) placing the solid support into the wound of the subject under conditions such that the healing of the wound is promoted.

The present invention also contemplates a method of screening candidate invasion-inducing agents comprising: a) providing: i) inducible cells, ii) a fibronectin-depleted substrate, and iii) one or more candidate invasion-inducing agents, b) contacting said cells in vitro with said fibronectin-free substrate and said one or more candidate invasion-inducing agents; and c) measuring the extent of cell invasion of said substrate. It is not intended that the present invention be limited to the type of inducible cells. In one embodiment, said inducible cells are epithelial cells. In another embodiment, said inducible cells are selected from the group consisting of fibroblasts, keratinocytes and muscle cells.

It is also not intended that the present invention be limited to a particular invasion-inducing agent. In one embodiment, said invasion-inducing agent comprises a fibronectin-derived peptide. In a preferred embodiment, said peptide comprises the amino acid sequence PHSRN (SEQ ID NO:1). In yet another embodiment, said peptide lacks the RGD (SEQ ID NO:81) motif. In yet another embodiment, said peptide lacks the motif which binds the ($\alpha5\beta1$) receptor.

It is not intended that the present invention be limited by the length of the peptide. In one embodiment, said peptide is between five and five hundred amino acids in length. In a preferred embodiment, said peptide comprises the amino acids PHSRN (SEQ ID NO:1) and additional amino acids added to the amino terminus. In another embodiment, said peptide comprises the amino acids PHSRN (SEQ ID NO:1) and additional amino acids added to the carboxy terminus. In yet another embodiment, said peptides comprises the amino acids PHSRN (SEQ ID NO:1) and additional amino acids added to both the amino and carboxy termini.

It is not intended that the present invention be limited to specific invasion-inducing agents. In one embodiment, the present invention contemplates invasion-inducing agents that comprise peptides that are protease resistant. In one embodiment, such protease-resistant peptides are peptides comprising protecting groups. In a preferred embodiment, endoprotease-resistance is achieved using peptides which comprise at least one D-amino acid.

DEFINITIONS

To facilitate understanding of the invention set forth in the disclosure that follows, a number of terms are defined below.

The term "wound" refers broadly to injuries to the skin and subcutaneous tissue initiated in different ways (e.g., pressure sores from extended bed rest and wounds induced by trauma) and with varying characteristics. Wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum). The term "partial thickness wound" refers to wounds that encompass Grades I–III; examples of partial thickness wounds include burn wounds, pressure sores, venous stasis ulcers, and diabetic ulcers. The term "deep wound" is meant to include both Grade III and Grade IV wounds. The present invention contemplates treating all wound types, including deep wounds and chronic wounds.

The term "chronic wound" refers to a wound that has not healed within 30 days.

The phrase "positioning the solid support in or on the wound" is intended to mean contacting some part of the wound with the solid support.

The phrases "promote wound healing," "enhance wound healing," and the like refer to either the induction of the formation of granulation tissue of wound contraction and/or the induction of epithelialization (i.e., the generation of new cells in the epithelium). Wound healing is conveniently measured by decreasing wound area.

The phrase "wound fluid contents" refers to liquid associated with a wound, as well as cells, cell factors, ions, macromolecules and protein material suspended such liquid at the wound site.

The term "subject" refers to both humans and animals.

The terms "enclosure," "compartment," and the like refer broadly to any container capable of confining a solid support within a defined location.

The term "solid support" refers broadly to any support, including, but not limited to, microcarrier beads, gels, "Band-Aids" and dressings.

The term "dressing" refers broadly to any material applied to a wound for protection, absorbance, drainage, etc. Thus, adsorbent and absorbent materials are specifically contemplated as a solid support. Numerous types of dressings are commercially available, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), and cellophane (cellulose with a plasticizer) [Kannon and Garrett, *Dermatol. Surg.* 21:583–590 (1995); Davies, *Burns* 10:94 (1983)]. The present invention specifically contemplates the use of dressings impregnated with the wound healing promoting and enhancing compounds of the present invention.

The term "biocompatible" means that there is minimal (i.e., no significant difference is seen compared to a control), if any, effect on the surroundings. For example, in some embodiments of the present invention, the dressing comprises a biocompatible membrane.

The term "peptide derivative" refers to compound having an imino group (—NH—), and more particularly, a peptide bond. Peptides may be regared as substituted amides. Like the amide group, the peptide bond shows a high degree of resonance stabilization. The C—N single bond in the peptide linkage has typically about 40 percent double-bond character and the C=O double bond about 40 percent single-bond character. "Protecting groups" are those groups which prevent undesirable reactions (such as proteolysis) involving unprotected functional groups. In one embodiment, the present invention contemplates that the protecting group is an acyl or an amide. In one embodiment, the acyl is acetate. In another embodiment, the protecting group is a benzyl group. In another embodiment, the protecting group is a benzoyl group. The present invention also contemplates combinations of such protecting groups.

The term "Band-Aid™" is meant to indicate a relatively small adhesive strip comprising and adsorbent pad (such as a gauze pad) for covering minor wounds.

GENERAL DESCRIPTION OF THE INVENTION

Figure 1:
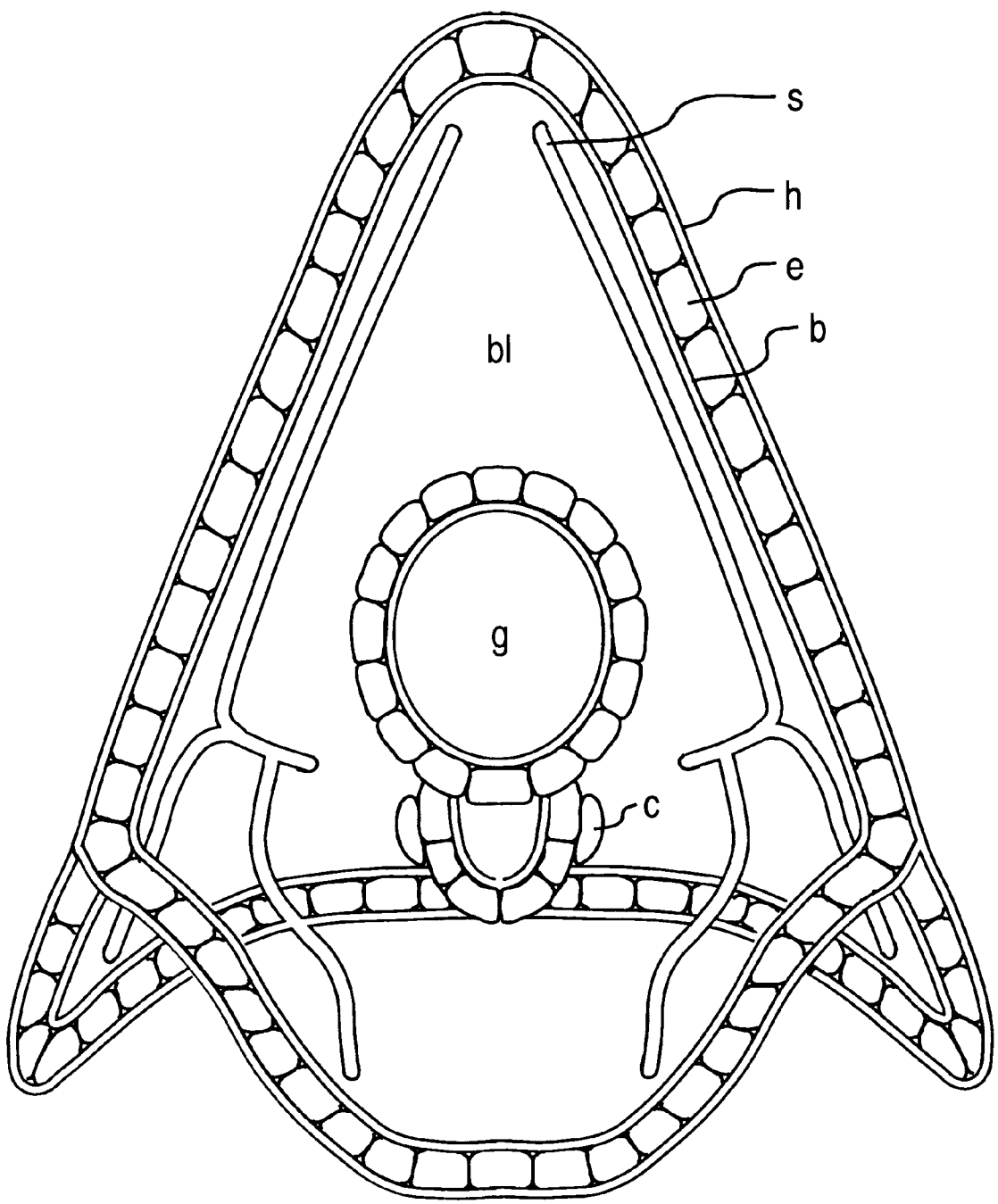
FIG. 1 schematically shows the one embodiment of the substrate used according to the present invention for testing invasion of cells (e.g. fibroblasts). The spatial relationship of the ectoderm of the *Strongylocentrotus purpuratus* embryo to its extracellular matrix and to blastocoelar structures are shown (s, spicules; h, hyalin layer; e, ectoderm; b, subectodermal basement membrane; bl, blastocoel; g, stomach of the primitive gut; c, coelomic pouches). The esophagus and intestine do not appear on the side of the embryo shown.

The therapy of wounds, particularly those which are made difficult to heal by disease, has been attempted with a variety of purified growth factors or cytokines because these molecules can induce cellular proliferation or increase the motility of cells in wounds. Thus, if presented in the correct form and location at the right time, growth factors may greatly accelerate or enhance the healing of wounds by stimulating the growth of new tissue. Given the complexity and clinical variability of wounds, an obvious difficulty with the application of specific, purified growth factors or cytokines to wounded tissue, alone or in combination, is that their forms or specific distributions in the wound may not support their normal activities. Instead, the effectiveness of growth factors and cytokines in promoting the healing of wounded tissue may depend on their secretion by fibroblasts or macrophages.

The present invention contemplates a more effective approach; this approach involves methods that stimulate the invasion of the wound by the cells which synthesize the growth factors and cytokines active in stimulating wound repair, especially monocytes, macrophages, keratinocytes, and fibroblasts. This strategy allows the cells in their normal in vivo setting to secrete the active factors. This approach has a number of advantages: (1) the temporal and spatial distributions of the factors are likely to be optimal because the normally active cells in their correct settings are secreting them; (2) all the appropriate factors are likely to be present in their active forms, irrespective of whether they have been identified or cloned; (3) the sequential effects of the factors in recruiting subsequent waves of cells involved in the healing process to the wound site are likely to be enhanced by the presence of more initiating cells in the wound. Thus, the present invention can be used to augment the effects of growth factor treatment.

The present invention is based on the discovery that the pure PHSRN (SEQ ID NO:1) peptide or purified plasma fibronectin fragments (i.e. fibronectin-derived peptides) containing it, and lacking the α4β1 integrin binding site in the IIICS region, are sufficient to stimulate fibroblast invasion of basement membranes in vitro under serum-free conditions, while intact plasma fibronectin fails to stimulate fibroblast invasion. This suggests that this peptide, or forms of it not subject to rapid proteolysis, may have similar effects on fibroblasts and monocytes/macrophages in vivo. Recruitment of fibroblasts or monocytes/macrophages whose paracrine, regulatory effects on a variety of neighboring cells are required for the early stages of wound healing is contemplated as a highly efficient and effective way to stimulate the cascade of regulatory interactions involved in wound healing because these cells will secrete the active factors or cytokines in the correct temporal sequences and spatial locations to ensure their optimal activities. PHSRN-containing (SEQ ID NO:1) peptides (or structurally related molecules) according to the present invention stimulate the entry of cells such as fibroblasts and monocyte/macrophages into the provisional matrix of a wound, so that the entering cells themselves secrete the factors and cytokines active in inducing or potentiating wound healing.

DESCRIPTION OF PREFERRED EMBODIMENTS

The present invention contemplates 1) assays to rapidly and readily assess both a) the invasion potential of cells of patients (such as burn or diabetes patients) as well as b) the potential of candidate inducing agents (such as non-peptide compounds having similar activity to PHSRN-containing (SEQ ID NO:1) peptides) and 2) compositions and methods for the treatment of patients with wounds.

A. Assays For Testing Invasion Potential And Screening New Therapeutics

It may be desirable to test the potential of cells for invasion, thereby predicting the ability of a patient to respond to the wound treatment according to the present invention. Similarly, it may be desirable to screen new potential therapeutics for their level of inducing activity. Two assay systems are contemplated for such testing.

1. Fibronectin-depleted Substrates

In one assay system, the present invention contemplates using fibronectin-depleted substrates. These are substrates that originally contain fibronectin that are treated according to the methods of the present invention (see below) to remove fibronectin. It is not intended that the present invention be limited by the nature of the original substrate; such fibronectin-containing substrates suitable for treatment and depletion include i) complex substrates containing a variety of extracellular proteins and ii) less complex substrates containing fibronectin along with one or two other proteins (e.g. collagen, laminin, etc.).

It is also not intended that the present invention be limited by the precise amount of fibronectin remaining after the substrate has been treated. In other words, while the methods of the present invention remove fibronectin, and in some embodiments, remove substantially all fibronectin, it is within the meaning of the term "fibronectin-depleted" substrate that a small amount of fibronectin remain in the substrate.

In one embodiment, the present invention contemplates using an extracellular matrix available commercially. For example, the present invention contemplates treating basement membrane matrices such as ECM GEL, a matrix from mouse sarcoma (commercially available from Sigma, St. Louis, Mo.). However, it is not intended that the present invention be limited by the particular fibronectin-containing substrate. For example, other commercially available substrates are contemplated, such as the commonly used substrate Matrigel (available from Becton Dickinson Labware, Catalog #40234); Matrigel can be treated appropriately according to the methods of the present invention so as to render it "fibronectin-depleted" (see below).

Consequently, the present invention contemplates a fibronectin-free substrate. In this embodiment, Matrigel is treated so that it is substantially fibronectin-free. The preparation of fibronectin-free Matrigel involves "panning" the Matrigel substrate on gelatin as well as "panning" the substrate on anti-fibronectin antibody (anti-human fibronectin IgG is available commercially, such as antibody from Promega Corporation, Madison, Wis.).

2. Naturally Occurring Fibronectin-free Substrates

In another embodiment, the present invention contemplates substrates that are naturally free of fibronectin; such a source provides, for example, basement membranes permeable to select types of normally invasive cells, such membranes being naturally serum-free. In one embodiment, the present invention contemplates sea urchins as a source of such membranes. In this regard, the ectoderm of sea urchin embryos is one cell thick, and secretes an underlying basement membrane (see FIG. 1) very similar to that of mammals. These embryos contain no circulatory or lymphatic systems; and thus, their basement membranes are serum-free. In embryos, the subectodermal basement membrane functions simultaneously as a migration substrate for several, specific mesenchymal cell types while it functions as an invasion substrate for others.

Sea urchin embryo basement membranes (SU-ECM) can be prepared by mild detergent treatment as described in D. Livant el al., *Cancer Research* 55:5085 (1995). Briefly, adult *Strongylocentrotus purpuratus* sea urchins can be obtained commercially (e.g. from Pacific BioMarine), and their embryos cultured to the early pluteus stage in artificial sea water at 15° C. SU-ECM are then prepared from them by treatment with nonionic detergent and srerilized by dilution in the appropriate media.

Cells for the invasion assay are harvested by rinsing in Hanks' balanced salt solution, followed by brief treatment with 0.25% trypsin, 0.02% EDTA, and pelleting and resuspension in the appropriate medium with or without 5% FCS at a density of about 50,000 cells per ml. When appropriate, purified bovine plasma fibronectin (Sigma), purified 120 kDa chymotryptic fragment (Gibco BRL) or PHSRN (SEQ ID NO:1) peptides (synthesized at the Biomedical Research Core Facilities of the University of Michigan) are added to the resuspended cells prior to placement of the cells on SU-ECM. In each well of a plate used for an invasion assay, SU-ECM were placed in 0.5 ml of the appropriate medium, and 0.5 ml of the resuspended cells dropped on their exterior surfaces. Invasion assays were incubated 1 to 16 hours prior to assay. If some circumstances, invasion assays were fixed in phosphate-buffered saline (PBS) with 2% formaldehyde for 5 minutes at room temperature, then rinsed into PBS.

Invasion assays are coded and scored blindly by microscopic examination under phase contrast at 200- and 400-fold magnification. Each cell contacting an SU-ECM is scored for its position relative to the exterior or interior surfaces. A cell is judged to have invaded if it is located on an interior surface below the focal plane passing through the upper surface of the SU-ECM, but above the focal plane passing through its lower surface. The minimum viability of the cells in each assay is always ascertained at the time of assay by determining the fraction of spread, adherent cells on the bottom of each well scored.

An invasion frequency is defined as the fraction of cells in contact with basement membranes which are located in their interiors at the time of assay. Thus, an invasion frequency of 1 denotes invasion by 100% of the cells in contact with basement membranes. Invasion frequencies are determined multiple times for each cell type assayed. For each type of cell assayed the mean and standard deviation of the invasion frequencies were calculated.

Regardless of which of the two types of substrates are employed, the invasion substrates of the present invention are easy to prepare and give rapid, highly consistent results with a variety of cells, including but not limited to fibroblasts and keratinocytes. While not limited to any mechanism, it is believed that cells exposed to invasion-inducing agents in this manner are potentially rendered capable of invading the substrate. Again, while not limited to any mechanism, it is believed that the invasion inducing agent comprising the sequence PHSRN (SEQ ID NO:1) binds to the α5β1 receptor on the cell and thereby induces invasion of the substrate. In this regard, the present invention provides a method of treating cells comprising: a) providing i) cells expressing the α5β1 receptor, ii) a fibronectin-free substrate, and iii) one or more invasion-inducing agents; b) culturing said cells in serum-free culture media on said substrate in the presence of said invasion-inducing agents; and d) measuring the extent of cell invasion of said substrate. In one embodiment, the cells are human fibroblasts.

B. Compositions and Methods for the Treatment of Patients with Wounds

It is not intended that the present invention be limited by the nature of the wound healing promoting agent. Such agents can be identified functionally by simply testing them in the above-described in vitro assays. The extent of invasion of fibroblasts (or other suitable cells) with such agents is predictive of in vivo efficacy. Thus, the present invention contemplates in vivo treatment with "invasion-inducing agents," i.e. those agents which have the capability of causing invasion of cells (such as fibroblasts and keratinocytes) in the above-described in vitro assays.

1. Peptide Derivatives

In one embodiment, the invasion-inducing agent comprises a peptide derived from fibronectin. In a preferred embodiment, said peptide comprises the sequence PHSRN (SEQ ID NO:1). Of course, the peptide may be larger than five amino acids; indeed, the peptide fragment of fibronectin may contain hundreds of additional residues (e.g. five hundred amino acids). One such larger peptide is set forth in U.S. Pat. No. 5,492,890 (hereby incorporated by reference). In one embodiment, the PHSRN-containing peptide is less than one hundred amino acids in length and lacks the RGD (SEQ ID NO:81) sequence characteristic of fibronectin. A variety of PHSRN-containing peptides are contemplated, including the PHSRN (SEQ ID NO:1) peptide itself and related peptides where additional amino acids are added to the carboxy terminus, including (but not limited to) peptides comprising the sequence: 1) PHSRN (SEQ ID NO:1), 2) PHSRNS (SEQ ID NO:3), 3) PHSRNSI (SEQ ID NO:4), 4) PHSRNSIT (SEQ ID NO:5), 5) PHSRNSITL (SEQ ID NO:6), 6) PHSRNSITLT (SEQ ID NO:7), 7) PHSRNSITLTN (SEQ ID NO: 8) 8) PHSRNSITLTNL (SEQ ID NO:9), 9) PHSRNSITLTNLT (SEQ ID NO:10), 10) PHSRNSITLTNLTP (SEQ ID NO:11), and 11) PHSRNSITLTNLTPG (SEQ ID NO:12). Alternatively, PHSRN-containing (SEQ ID NO:1) peptides are contemplated where amino acids are added to the amino terminus, including (but not limited to) peptides comprising the sequence: 1) PEHFSGRPREDRVPIJSRN, (SEQ ID NO:13) 2) EHFSGRPREDRVPHSRN, (SEQ ID NO:14) 3)

HFSGRPREDRVPHSRN, (SEQ ID NO:15) 4) FSGRPREDRVPHSRN, (SEQ ID NO:16) 5) SGRPREDRVPHSRN, (SEQ ID NO:17) 6) GRPREDRVPHSRN, (SEQ ID NO:18) 7) RPREDRVPHSRN, (SEQ ID NO:19) 8) PREDRVPHSRN, (SEQ ID NO:20) 9) REDRVPHSRN, (SEQ ID NO:21) 10) EDRVPHSRN, (SEQ ID NO:22) 11) DRVPHSRN, (SEQ ID NO:23) 12) RVPHSRN, (SEQ ID NO:24) and 13) VPHSRN (SEQ ID NO:25). Finally, the present invention contemplates PHSRN-containing (SEQ ID NO:1) peptides where amino acids are added to both the amino and carboxy termini, including (but not limited to) peptides comprising the sequence PEHFSGRPREDRVPHSRNSITLTNLTPG, (SEQ ID NO:26) as well as peptides comprising portions or fragments of the PHSRN-containing (SEQ ID NO:1) sequence PEHFSGRPREDRVPHSRNSITLTNLTPG (SEQ ID NO:26).

Peptides containing variations on the PHSRN (SEQ ID NO:1) motif are contemplated. For example, the present invention also contemplates PPSRN-containing (SEQ ID NO:27) peptides for use in the above-named assays. Such peptides may vary in length in the manner described above for PHSRN-containing (SEQ ID NO:1) peptides. Alternatively, PPSRN (SEQ ID NO:27) may be used as a peptide of five amino acids.

Similarly, peptides comprising the sequence -HHSRN- (SEQ ID NO:28), -HPSRN-(SEQ ID NO:29), -PHTRN- (SEQ ID NO:30), -HHTRN-(SEQ ID NO:31), -HPTRN- (SEQ ID NO:32), -PHSNN-(SEQ ID NO:33), -HHSNN- (SEQ ID NO:34), -HPSNN-(SEQ ID NO:35), -PHTNN- (SEQ ID NO:36), -HHTNN-(SEQ ID NO:37), -HPTNN- (SEQ ID NO:38), -PHSKN-(SEQ ID NO:39), -HHSKN- (SEQ ID NO:40), -HPSKN-(SEQ ID NO:41), -PHTKN- (SEQ ID NO:42), -HHTKN-(SEQ ID NO:43), -HPTKN- (SEQ ID NO:44), -PHSRR-(SEQ ID NO:45), -HHSRR- (SEQ ID NO:46), -HPSRR-(SEQ ID NO:47), -PHTRR- (SEQ ID NO:48), -HHTRR-(SEQ ID NO:49), -HPTRR- (SEQ ID NO:50), -PHSNR-(SEQ ID NO:51), -HHSNR- (SEQ ID NO:52), -HPSNR-(SEQ ID NO:53), -PHTNR- (SEQ ID NO:54), -HHTNR-(SEQ ID NO:55), -HPTNR- (SEQ ID NO:56), -PHSKR-(SEQ ID NO:57), -HHSKR- (SEQ ID NO:58), -HPSKR-(SEQ ID NO:59), -PHTKR- (SEQ ID NO:60), -HHTKR-(SEQ ID NO:61), -HPTKR- (SEQ ID NO:62), -PHSRK-(SEQ ID NO:63), -HHSRK- (SEQ ID NO:64), -HPSRK-(SEQ ID NO:65), -PHTRK- (SEQ ID NO:66), -HHTRK-(SEQ ID NO:67), -HPTRK- (SEQ ID NO:68), -PHSNK-(SEQ ID NO:69), -HHSNK- (SEQ ID NO:70), -HPSNK-(SEQ ID NO:71), -PHTNK- (SEQ ID NO:72), -HHTNK-(SEQ ID NO:73), -HPTNK- (SEQ ID NO:74), -PHSKK-(SEQ ID NO:75), -HHSKK- (SEQ ID NO:76), -HPSKK-(SEQ ID NO:77), -PHTKK- (SEQ ID NO:78), -HHTKK-(SEQ ID NO:79), or -HPTKK- (SEQ ID NO:80) are contemplated by the present invention. Such peptides can be used as five amino acid peptides or can be part of a longer peptide (in the manner set forth above for PHSRN-containing (SEQ ID NO:1) peptides).

As noted above, the present invention contemplates peptides that are protease resistant. In one embodiment, such protease-resistant peptides are peptides comprising protecting groups. In a preferred embodiment, the present invention contemplates a peptide containing the sequence PHSRN (SEQ ID NO:1) (or a variation as outlined above) that is protected from exoproteinase degradation by N-terminal acetylation ("Ac") and C-terminal amidation. The Ac-XPHSRNX-NH$_2$ (SEQ ID NO:84) peptide (which may or may not have additional amino acids, as represented by X; the number of additional amino acids may vary from between 0 and 100, or more) is useful for in vivo administration because of its resistance to proteolysis.

In another embodiment, the present invention also contemplates peptides protected from endoprotease degradation by the substitution of L-amino acids in said peptides with their corresponding D-isomers. It is not intended that the present invention be limited to particular amino acids and particular D-isomers. This embodiment is feasible for all amino acids, except glycine; that is to say, it is feasible for all amino acids that have two stereoisomeric forms. By convention these mirror-image structures are called the D and L forms of the amino acid. These forms cannot be interconverted without breaking a chemical bond. With rare exceptions, only the L forms of amino acids are found in naturally occurring proteins. In one embodiment, the present invention contemplates PHS(dR)N-containing (SEQ ID NO:86) peptides for wound healing 2. Mimetics Compounds mimicking the necessary conformation for recognition and docking to the receptor binding to the peptides of the present invention are contemplated as within the scope of this invention. For example, mimetics of PHSRN (SEQ ID NO:1) peptides are contemplated. A variety of designs for such mimetics are possible. For example, cyclic PHSRN-containing (SEQ ID NO:1) peptides, in which the necessary conformation for binding is stabilized by nonpeptides, are specifically contemplated. U.S. Pat. No. 5,192,746 to Lobl, et al, U.S. Pat. No. 5,169,862 to Burke, Jr., et al, U.S. Pat. No. 5,539,085 to Bischoff, et al, U.S. Pat. No. 5,576,423 to Aversa, et al, U.S. Pat. No. 5,051,448 to Shashoua, and U.S. Pat. No. 5,559,103 to Gaeta, et al, all hereby incorporated by reference, describe multiple methods for creating such compounds.

Synthesis of nonpeptide compounds that mimic peptide sequences is also known in the art. Eldred, et al, (J. Med. Chem. 37:3882 (1994)) describe nonpeptide antagonists that mimic the Arg-Gly-Asp (SEQ ID NO:81) sequence. Likewise, Ku, et al, (J. Med. Chem. 38:9 (1995)) give further elucidation of the synthesis of a series of such compounds. Such nonpeptide compounds that mimic PHSRN (SEQ ID NO:1) peptides are specifically contemplated by the present invention.

The present invention also contemplates synthetic mimicking compounds that are multimeric compounds that repeat the relevant peptide sequence. In one embodiment of the present invention, it is contemplated that the relevant peptide sequence is Pro-His-Ser-Arg-Asn (SEQ ID NO:1) or Pro-Pro-Ser-Arg-Asn (SEQ ID NO:85); in another embodiment, the relevant peptide sequence is Ile-Lys-Val-Ala-Val (SEQ ID NO:2). As is known in the art, peptides can be synthesized by linking an amino group to a carboxyl group that has been activated by reaction with a coupling agent, such as dicyclohcxylcarbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the (α-amino group of the component containing the activated carboxyl group can be blocked with a tertbutyloxycarbonyl group. This protecting group can be subsequently removed by exposing the peptide to dilute acid, which leaves peptide bonds intact.

With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

In one embodiment, the mimetics of the present invention are peptides having sequence homology to the above-described PHSRN-containing (SEQ ID NO:1) peptides (including, but not limited to, peptides in which L-amino acids are replaced by their D-isomers). One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant. W. R. Pearson and D. J. Lipman, Proc. Natl. Acad. Sci. (USA), 85:2444–2448 (1988); D. J. Lipman and W. R. Pearson, *Science,* 227:1435–1441 (1985). In the present invention, synthetic polypeptides useful in wound healing are those peptides with statistically significant sequence homology and similarity (Z value of Lipman and Pearson algorithm in Monte Carlo analysis exceeding 6).

3. Formulations

It is not intended that the present invention be limited by the particular nature of the therapeutic preparation, so long as the preparation comprises an invasion-inducing agent. For example, such compositions can be provided together with physiologically tolerable liquid, gel or solid carriers, diluents, adjuvants and excipients.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as liquid solutions or suspensions, or in solid forms. Formulations for wound healing usually will include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%.

The compositions are also prepared as injectables, either as liquid solutions or suspensions; solid forms suitable for solution in, or suspension in, liquid prior to injection may also be prepared.

The invasion-inducing agents of the present invention are often mixed with diluents or excipients which are physiological tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); $\mu$ (micron); M (Molar); $\mu$M (micromolar); mM (millimolar); N (Normal); mol (moles); mmol (millimoles); $\mu$mol (micromoles); nmol (nanomoles); g (grams); mg (milligrams); $\mu$g (micrograms); ng (nanograms); L (liters); ml (milliliters); $\mu$l (microliters); cm (centimeters); mm (millimeters); $\mu$m (micrometers); nM (nanomolar); ° C. (degrees Centigrade); mAb (monoclonal antibody); MW (molecular weight); PBS (phophate buffered saline); U (units); d (days).

In some of the examples below, wounds are created in animals. Briefly, in one approach, experimental wounds were created in animals which were pre-anesthetized by inhalation of metofane and intradermal injection of lidocane. The hair on the backs of the animals was clipped and the skin was disinfected with 70% ethanol. A piece of skin was then removed from the disinfected site with a 4 mm punch biopsy.

EXAMPLE 1

Production of Fibronectin-free Substrates

This example describes a purification approach for removal of plasma fibronectin (and/or cellular fibronectin) from a substrate (Matrigel). In this example, removal was attempted by affinity chromatography over Gelatin-Sepharose (a technique which can be used to remove plasma fibronectin from fetal calf serum).

The Gelatin-Sepharose beads were obtained from Pharmacia (Catalog# 17-0956-01). Two Kontes columns were set up with about 2 mls of Gelatin-Sepharose beads at 4 C. to prevent gelling of the Matrigel. The columns were then rinsed with about 10 column volumes of PBS to remove the preservative from the beads. The columns were drained to the top of the beads; then Matrigel was carefully added to the column. Once the Matrigel had entered the column, PBS was added to the top of the column. The Matrigel which was passed over the first column was collected and passed over the second column. The fibronectin-depleted Matrigel collected from the second column was plated on 48-well plates (150 $\mu$l/well), sterilized under a UV light for 10 minutesand incubated at 37 C. overnight. The Matrigel treated in this manner failed to form a gel at 37 C.

EXAMPLE 2

Production of Fibronectin-free Substrates

This example describes a purification approach for removal of plasma fibronectin (and/or cellular fibronectin) from a substrate (Matrigel). In this example, removal was attempted by successive panning on gelatin. Eight wells of 24-well plate were coated with a 2% gelatin solution (the gelatin was obtained from Becton Dickinson Labware, Catalog #11868). The wells were filled with the gelatin solution which had been heated to 50 C. and incubated for 3 minutes. Then the solution was removed and the wells were allowed to air dry. Following drying, the wells were thoroughly rinsed with $H_2O$ followed by two rinses with PBS. The plates were again allowed to dry; thereafter they were stored at −20 C. until use. Matrigel was thawed on ice and then added to one of the wells of a gelatin-coated plate (between 800 $\mu$l and 1 ml of Matrigel was added to a well of a 24-well plate). The plate was placed in a bucket of ice in a 4 C. room on an orbital shaker where the Matrigel was incubated in the well for two hours (although overnight incubation can be used). Following the incubation, the Matrigel was moved from the first well to a second well and then incubated for two hours under the same conditions. This process was repeated until the Matrigel had been incubated on all eight wells of the gelatin-coated plate.

Following the depletion of the Matrigel, it was collected in Eppendorf tubes. It was then plated on a 48-well plate 150 µl/well), sterilized under a UV light for 10 minutes and incubated at 37 C. overnight. The Matrigel formed as gel and the following day, cells were added to each well.

EXAMPLE 3

Production of Fibronectin-free Substrates

This example describes a purification approach for removal of plasma fibronectin (and/or cellular fibronectin) from a substrate (Matrigel). In this example, removal was attempted by gelatin panning followed by antibody panning.
Anti-fibronectin Antibody-coated Wells
Wells of a 24-well plate were coated with an anti-fibronectin antibody. A mouse monoclonal antibody to human fibronectin was obtained from Oncogene Science (Catalog #CP13). Each well was incubated with 1 ml of antibody at a concentration of 30 µl/ml for 2 hours at room temperature. Each well was then incubated with a solution of 3% BSA in PBS for 2 hours at room temperature. Following the two incubation periods, the wells were thoroughly washed with PBS and stored at −20 C. until use.
Depleting Matrigel of Fibronectin
Matrigel was panned over eight gelatin-coated wells (as described above in Example 2) to remove most of the fibronectin and its fragments. Thereafter, the Matrigel was placed in the antibody-coated wells to remove any remaining fragments of fibronectin which contain the cell-binding domain but not the gelatin-binding domain. The Matrigel was incubated in an ice bucket on an orbital shaker at 4 C. for 2 hours. Once the Matrigel was depleted, it was collected in Eppendorf tubes. The fibronectin-depleted Matrigel was plated on a 48-well plate (150 µl/well), sterilized under a UV light for 10 minutes and incubated at 37 C. overnight. The Matrigel formed a gel and the following day, cells were added to the wells.

EXAMPLE 4

Improving Gelatin Depletion As Measured By Fibroblast Invasiveness

Figure 2:
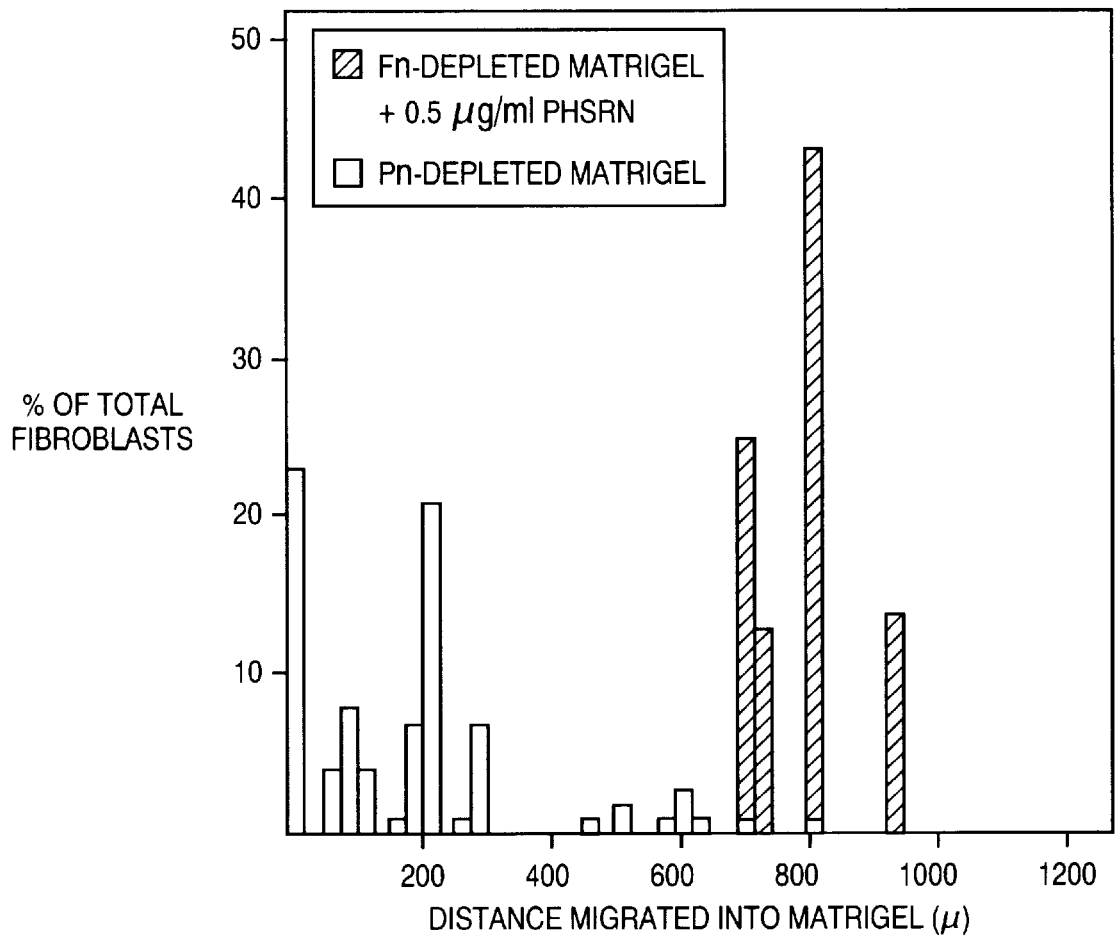
FIG. 2 is a graph showing the results of the testing of fibroblasts on fibronectin-depleted substrates in vitro with and without invasion-inducing agents according one embodiment of the method of the present invention.

In this example, normal, neonatal fibroblasts were tested on the depleted Matrigel material prepared according to Example 3 above (i.e. antibody depletion). As shown in FIG. 2, panning with an antibody after gelatin depletion improved the method for removal, as measured by the reduced invasiveness of fibroblasts. On the other hand, invasiveness of the fibroblasts could be induced by the addition of the PHSRN (SEQ ID NO:1) peptide. The success of antibody panning suggests the feasibility of removing other components by the antibody panning methods. Other serum components, such as thrombospondin, growth factors and cytokines are contemplated by the present invention for removal by the appropriate (commercially available) antibody.

EXAMPLE 5

Conjugation of PHSRN-containing (SEQ ID NO:1) peptides

In this example, the preparation of a peptide conjugate is described. The synthetic peptide $NH_2$-PHSRNC (SEQ ID NO:82) can be prepared commercially (e.g. Multiple Peptide Systems, San Diego, Calif.). The cysteine is added to facilitate conjugation to other proteins. In order to prepare a protein for conjugation (e.g. BSA), it is dissolved in buffer (e.g., 0.01 M $NaPO_4$, pH 7.0) to a final concentration of approximately 20 mg/ml. At the same time n-maleimidobenzoyl-N-hydroxysuccinimide ester ("MBS" available from Pierce) is dissolved in N,N-dimethyl formamide to a concentration of 5 mg/ml. The MBS solution, 0.51 ml, is added to 3.25 ml of the protein solution and incubated for 30 minutes at room temperature with stirring every 5 minutes. The MBS-activated protein is then purified by chromatography on a Bio-Gel P-10 column (Bio-Rad; 40 ml bed volume) equilibrated with 50 mM $NaPO_4$, pH 7.0 buffer. Peak fractions arc pooled (6.0 ml).

The above-described cysteine-modified peptide (20 mg) is added to the activated protein mixture, stirred until the peptide is dissolved and incubated 3 hours at room temperature. Within 20 minutes, the reaction mixture becomes cloudy and precipitates form. After 3 hours, the reaction mixture is centrifuged at 10,000 ×g for 10 min and the supernatant analyzed for protein content. The conjugate precipitate is washed three times with PBS and stored at 4° C.

EXAMPLE 6

Effect of Serum on PHSRN (SEQ ID NO:1 ) on Induction of Human Fibroblast Invasion In this example, the invasiveness of neonatal fibroblasts into an SU-ECM invasion substrate is considered. Experiments were performed under serum-free conditions, or in medium with 10% fetal calf serum (FCS). Neither serum-free medium nor medium containing serum supported fibroblast invasion. However, consistent with the induction of metalloproteinase gene transcription by the 120 kDa fragment of plasma fibronectin (pFn) containing the cell-binding domain, the 120 kDa fragment induced fibroblast invasion in the presence or in the absence of serum.

Figure 3B:
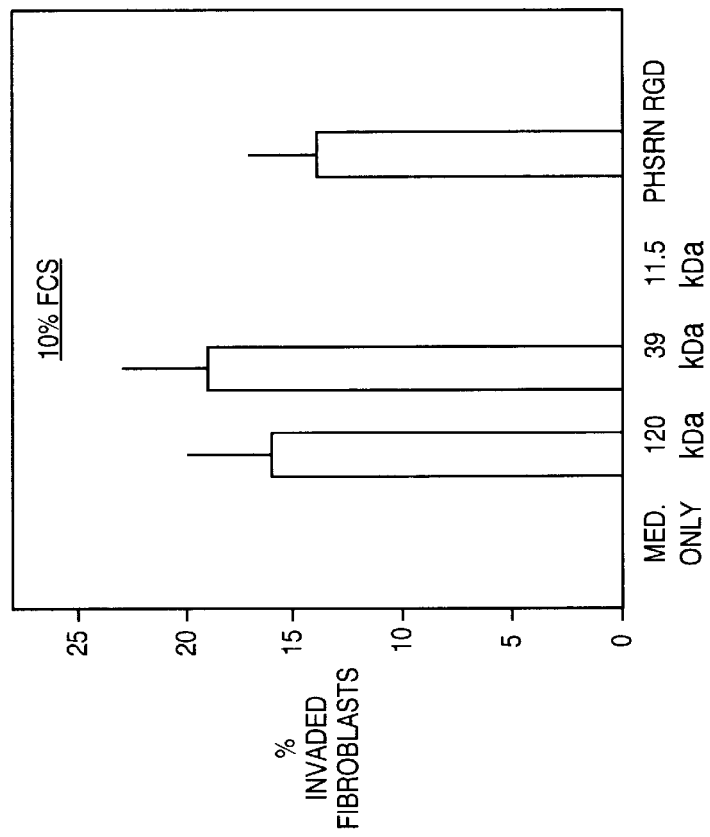
FIGS. 3A and 3B are graphs showing the percentages of invaded neonatal fibroblasts, corresponding to various fragments of the plasma fibronectin cell binding domain, after placement on an invasion substrates. The 120 kDa and 39 kDa fragments contain the PHSRN (SEQ ID NO:1) sequence. The 11.5 kDa fragment does not. These fragments lack the $\alpha4\beta1$ integrin binding site in the IIICS region.
Figure 3A:
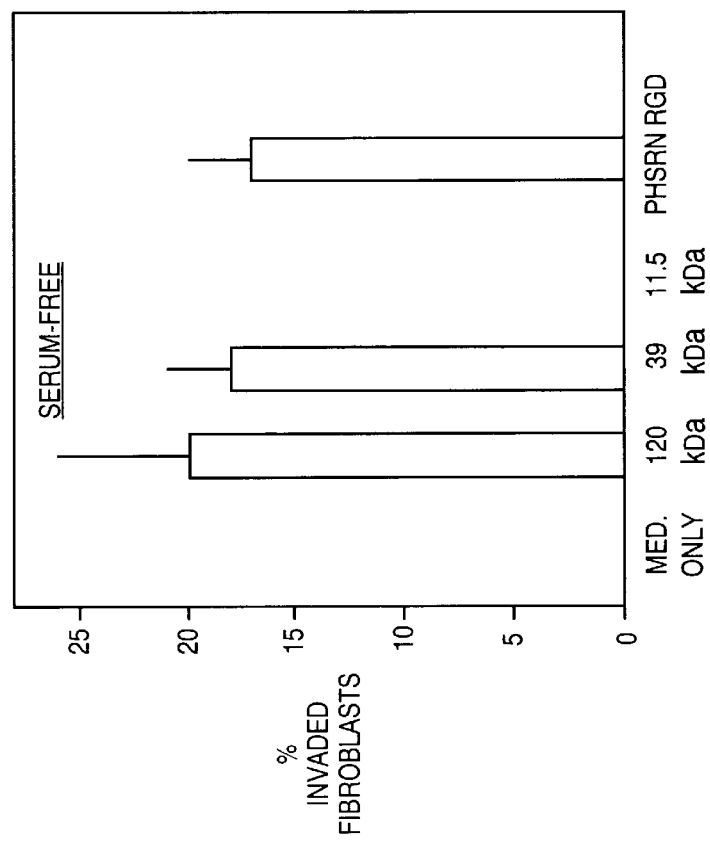

To insure the induction of invasion documented in these experiments was due to pFn sequences, and not to bound growth factors or cytokines, all of the fragments used were purified by electrophoresis on denaturing gels, followed by electoelution. Also, all fragments and sequences tested here present in solution at a molar concentration equivalent to that of plasma fibronectin in serum. The 120 kDa cell binding domain consists of modules 2 through 11. Modules 9 and 10 are bound by the ($\alpha 5\beta 1$) receptor because module 9 contains the PHSRN (SEQ ID NO:1) sequence, while module 10 has the RGD sequence (SEQ ID NO:81). Accordingly, the invasion-inducing activities of a gel-purified 39 kDa fragment containing modules 7–9 (and the PHSRN (SEQ ID NO:1) sequence) with a gel-purified 11.5 kDa fragment containing module 10 (and the RGD(SEQ ID NO:81)) sequence was considered. As can be seen in FIGS. 3A and 3B, all of the invasion-inducing activity of the plasma fibronectin cell-binding domain appeared to map to the 39 kDa fragment bearing modules 7–9 and the PHSRN (SEQ ID NO:1) sequence. To test this observation rigorously, the PHSRN (SEQ ID NO:1) peptide, which was synthesized in a peptide synthesis CORE facility, and the GRGDS (SEQ ID NO:83) peptide, which was obtained commercially, were tested in the presence or in the absence of serum for their invasion-inducing activities. As shown in FIG. 3, the PHSRN (SEQ ID NO:1) sequence contained all the invasion-stimulatory activity of the pFn cell-binding domain; and the RGD (SEQ ID NO:81) sequence had no detectable activity at the near-physiological concentrations used.

EXAMPLE 7

Dose-response Effect Between PHSRN (SEQ ID NO:1) Concentration and Fibroblast Invasion.

Figure 4:
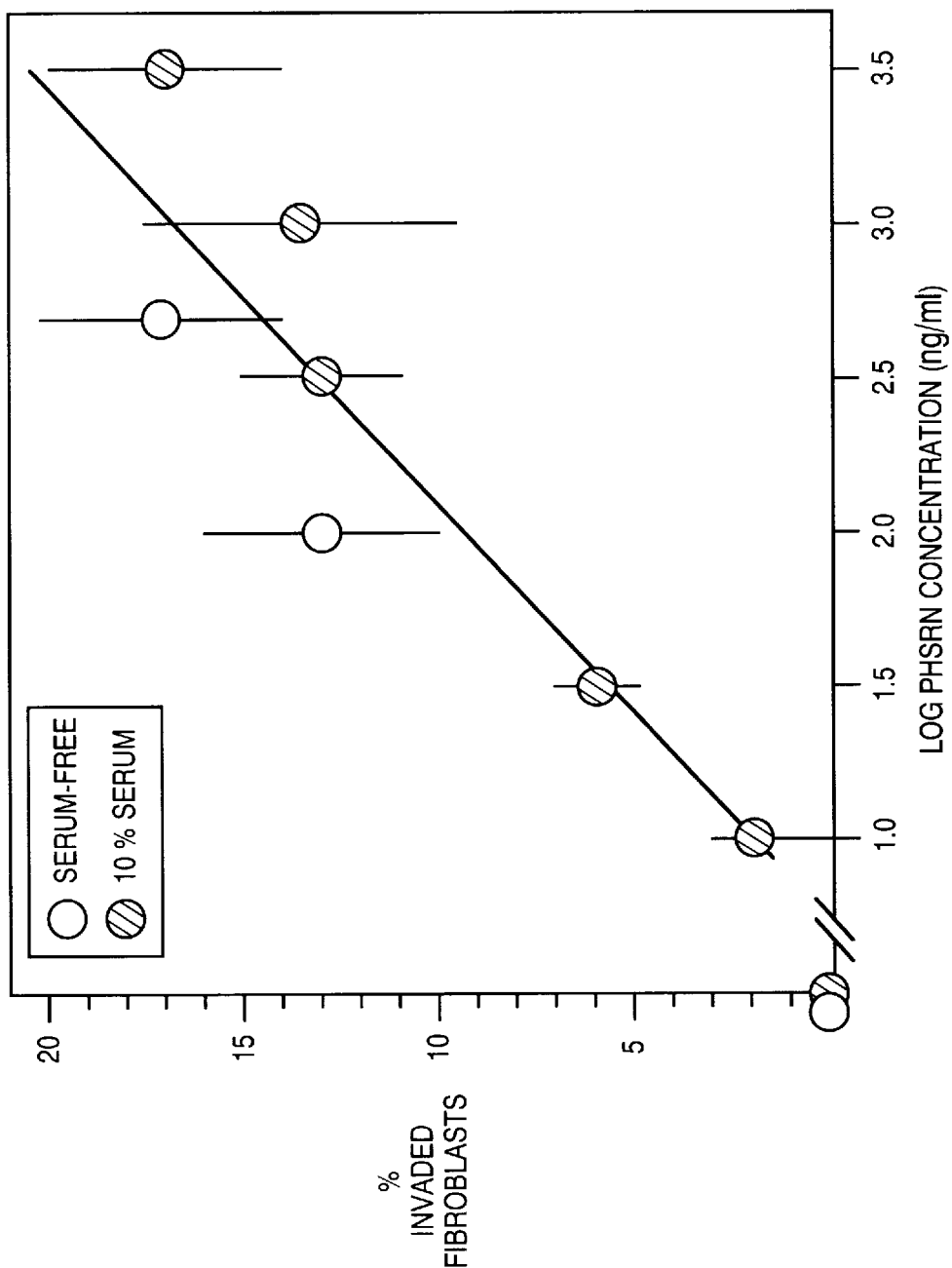
FIG. 4 is a graph presenting a dose response curve relating concentration of peptides containing the amino acid sequence PHSRN (SEQ ID NO:1) to fibroblast invasion into an invasion substrate.

In this example, fibroblasts were induced to invade SU-ECM by concentrations of the PHSRN (SEQ ID NO:1) peptide ranging from 10 to 3000 ng per ml in the presence, or in the absence of serum. As can be seen from the dose response curves shown in FIG. 4, the PHSRN (SEQ ID NO:1) peptide was able to induce fibroblast invasion in the presence of serum, which has been found to contain 40 to 80 micrograms per ml of intact plasma fibronectin, and in its absence in a similar log-linear fashion. D. F. Mosher "Physiology of Fibronectin" *Ann. Rev. Med.* 35:561 (1984).

These data suggest the metalloproteinase gene repressors produced by fibroblast α4β1 and α5β1binding of intact plasma fibronectin do not appear to bind with such high affinity that they stop PHSRN-mediated (SEQ ID NO:1) invasion induction in the presence of serum. P. Huhtala et al. "Cooperative Signaling by α5β1 and α4β1 Integrins Regulates Metalloproteinase Gene Expression in Fibroblasts Adhering to Fibronectin" *J. Cell Biol.* 129: 867 (1995). This observation is consistent with the fact that, although induced by fibronectin fragments, fibroblast invasion in vivo must occur in the presence of intact plasma fibronectin.

EXAMPLE 8

Figure 5:
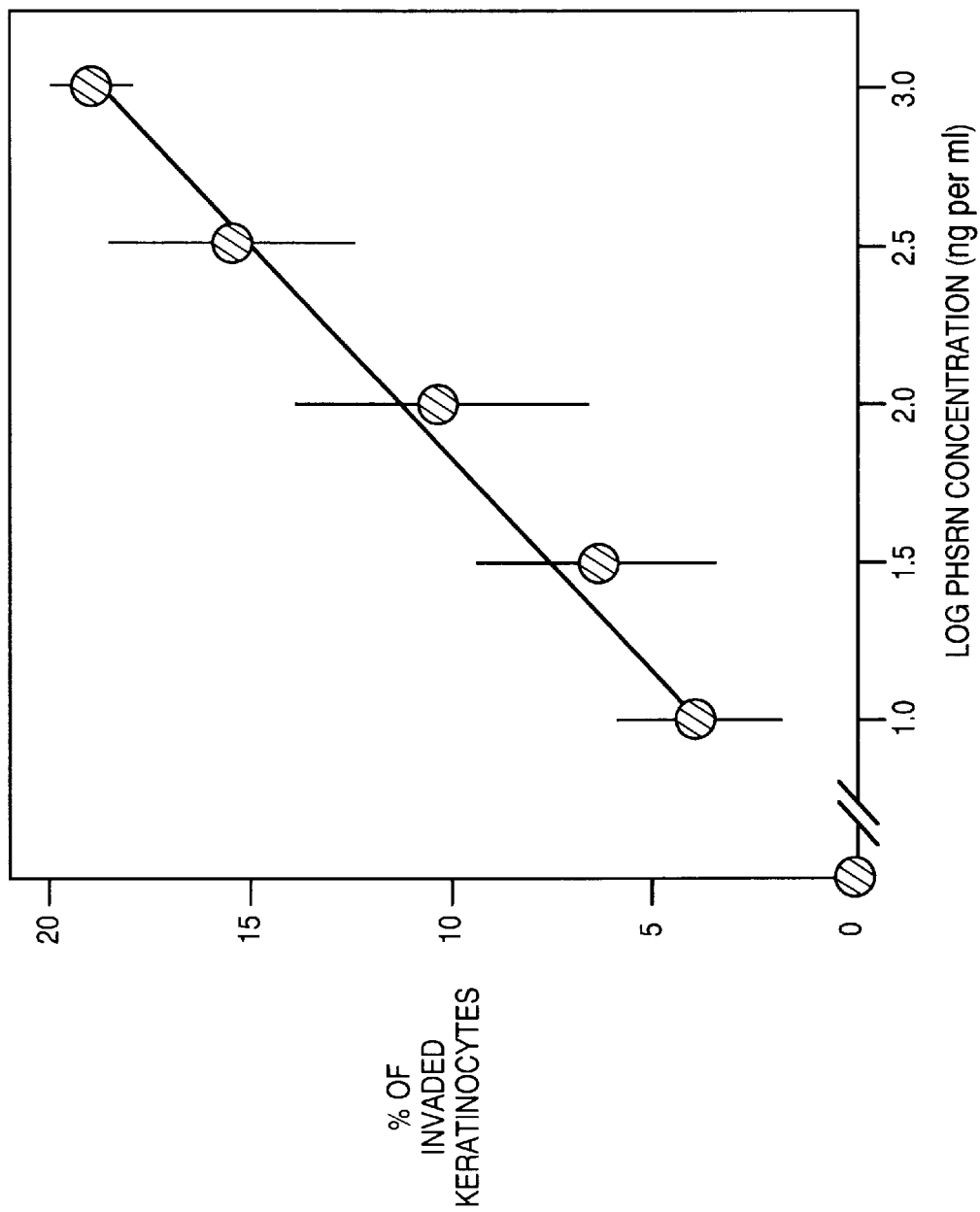
FIG. 5 is a graph presenting a dose response curve relating concentration of peptides containing the amino acid sequence PHSRN (SEQ ID NO:1) to keratinocyte invasion into an invasion substrate.

Induction of Keratinocyte Invasion by PHSRN (SEQ ID NO:1) in the Presence of Serum In this example the induction of normal keratinocyte invasion by PHSRN (SEQ ID NO:1) peptide, in the presence of serum, is presented. Normal neonatal keratinocytes were tested for their ability to be induced to invade SU-ECM by the PHSRN (SEQ ID NO:1) peptide. It is notable that the profile of keratinocyte invasive induction into SU-ECM by PHSRN (SEQ ID NO:1), presented in FIG. 5, is similar to the profile of invasive induction of fibroblast presented in Example 7. These data present the maximal invasion percentages for keratinocytes at a level of about 20%. Treatment of the cells (e.g. trypsin treatment) and assay conditions (e.g. time or orientation) are likely to effect this level. In any event, it is preferred that measurements are taken in the linear range.

EXAMPLE 9

Invasiveness of Normal Human Mammary or Prostate Epithelial Cell in

Response to Induction By PHSRN (SEQ ID NO:1) in a Serum Containing Environment

Figure 6:
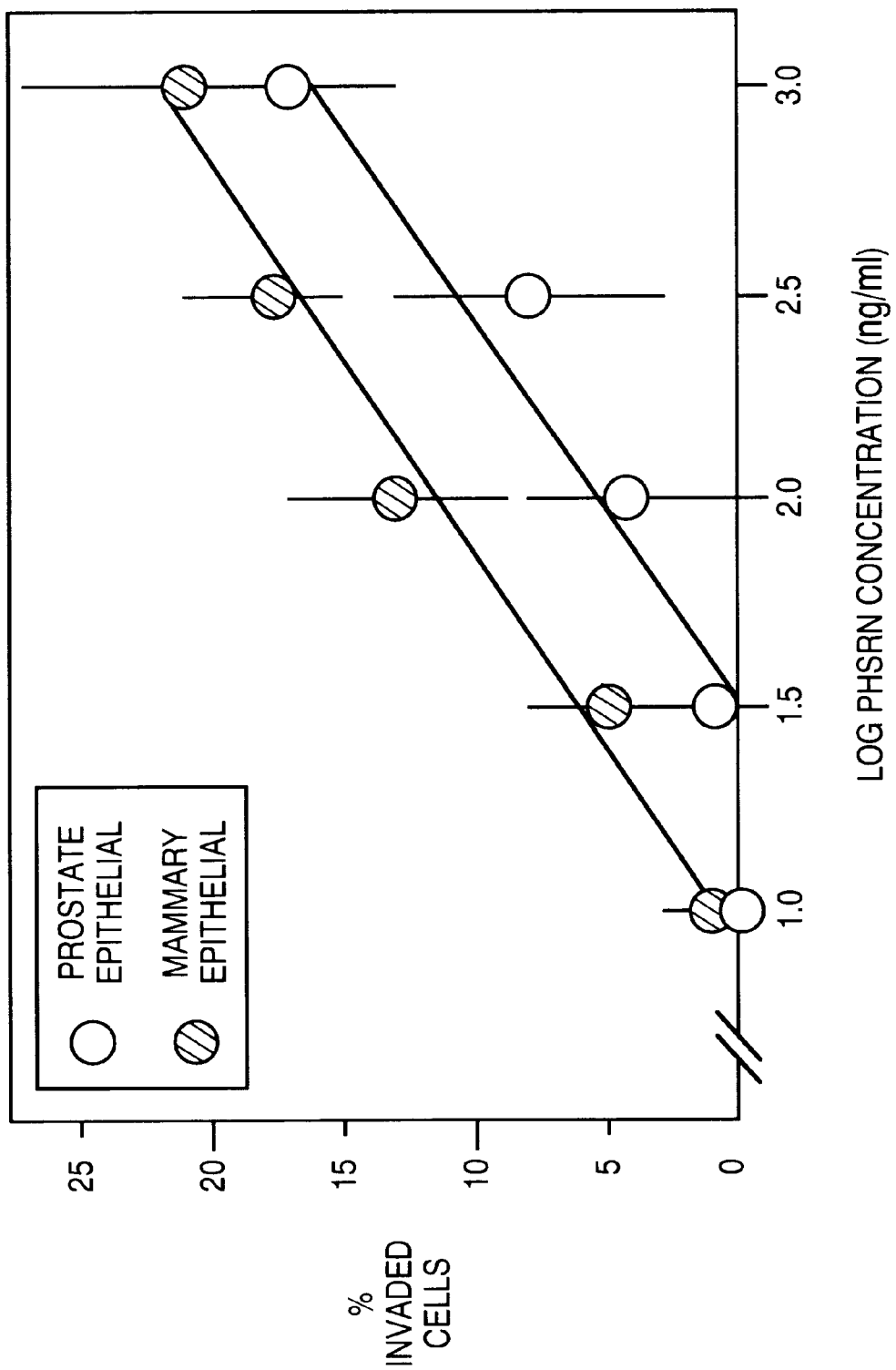
FIG. 6 is a graph presenting a dose response curve relating concentration of peptides containing the amino acid sequence PHSRN (SEQ ID NO:1) to human mammary or prostate epithelial cell invasion into an invasion substrate.

In this example, data is presented, FIG. 6, demonstrating that PHSRN (SEQ ID NO:1) peptide also induces the invasive behaviors of human mammary or prostate epithelial cells. These experiments were conducted in a serum containing environment using SU-ECM as an invasion substrate. As with fibroblasts, immunostaining experiments showed that mammary and prostate epithelial cells express both the α5β1 and the α4β1fibronectin receptors (not shown); thus the ability of the α5β1receptor to bind the PHSRN (SEQ ID NO:1) sequence on fibronectin fragments lacking the α4β1 binding site, which are generated in wounds may induce these epithelial cells to migrate into the provisional matrix or into its adjacent stroma to begin wound reepithelialization.

EXAMPLE 10

Figure 7:
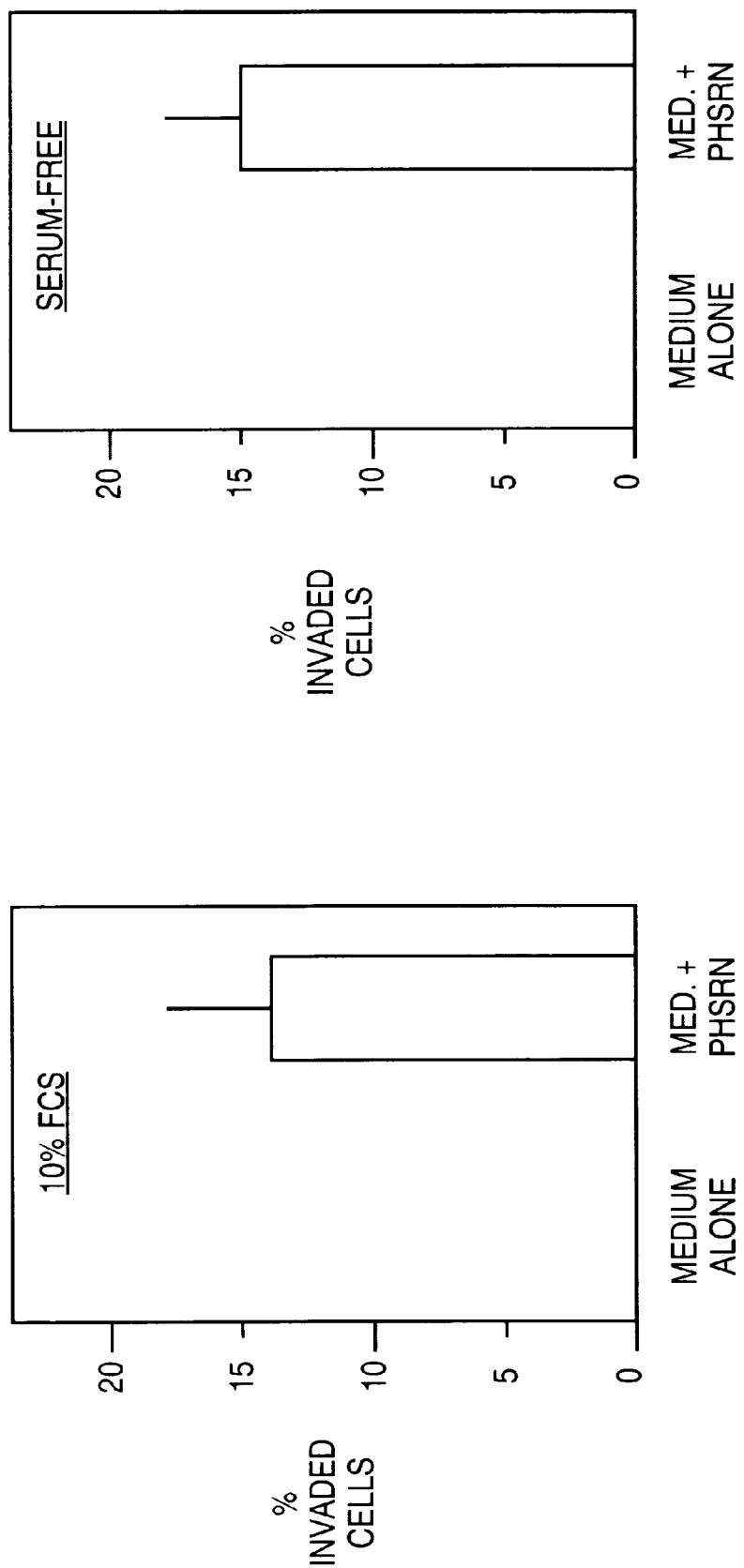
FIGS. 7A and 7B are graphs presenting the inductive effect of peptides containing the amino acid sequence PHSRN (SEQ ID NO:1) on mouse muscle satellite cell invasion into an invasion substrate.

Invasiveness of Mouse Muscle Satellite Cells in Response to induction by PHSRN (SEQ ID NO:1) in a Serum Containing Environment In this example, the ability of the PHSRN (SEQ ID NO:1) peptide to induce the invasive behavior of a third major tissue type, muscle cells, was considered. Mouse muscle satellite cells, which function as stem cells for muscle in vivo, were obtained from the laboratory of Dr. K. Kurachi (Department of Human Genetics). These cells were placed on SU-ECM invasion substrates in 1 microgram per ml of PHSRN (SEQ ID NO:1) peptide in the presence or absence of serum. As shown in FIGS. 7A and 7B, PHSRN (SEQ ID NO:1) induced the invasion of SU-ECM by muscle satellite cells. Since muscle satellite cells are normally located inside the basement membranes surrounding the muscle fibers, in direct contact with muscle cells, and since genetically engineered muscle cells have so far failed to cross the basement membranes separating them from the muscle fibers in vivo, it is interesting to speculate that treatment with the PHSRN (SEQ ID NO:1) invasion-inducing peptide may induce muscle satellite cell migration into muscle in vivo, where these cells might resume normal function.

EXAMPLE 11

In Vivo Effect of PHSRN (SEQ ID NO:1)

Figure 8:
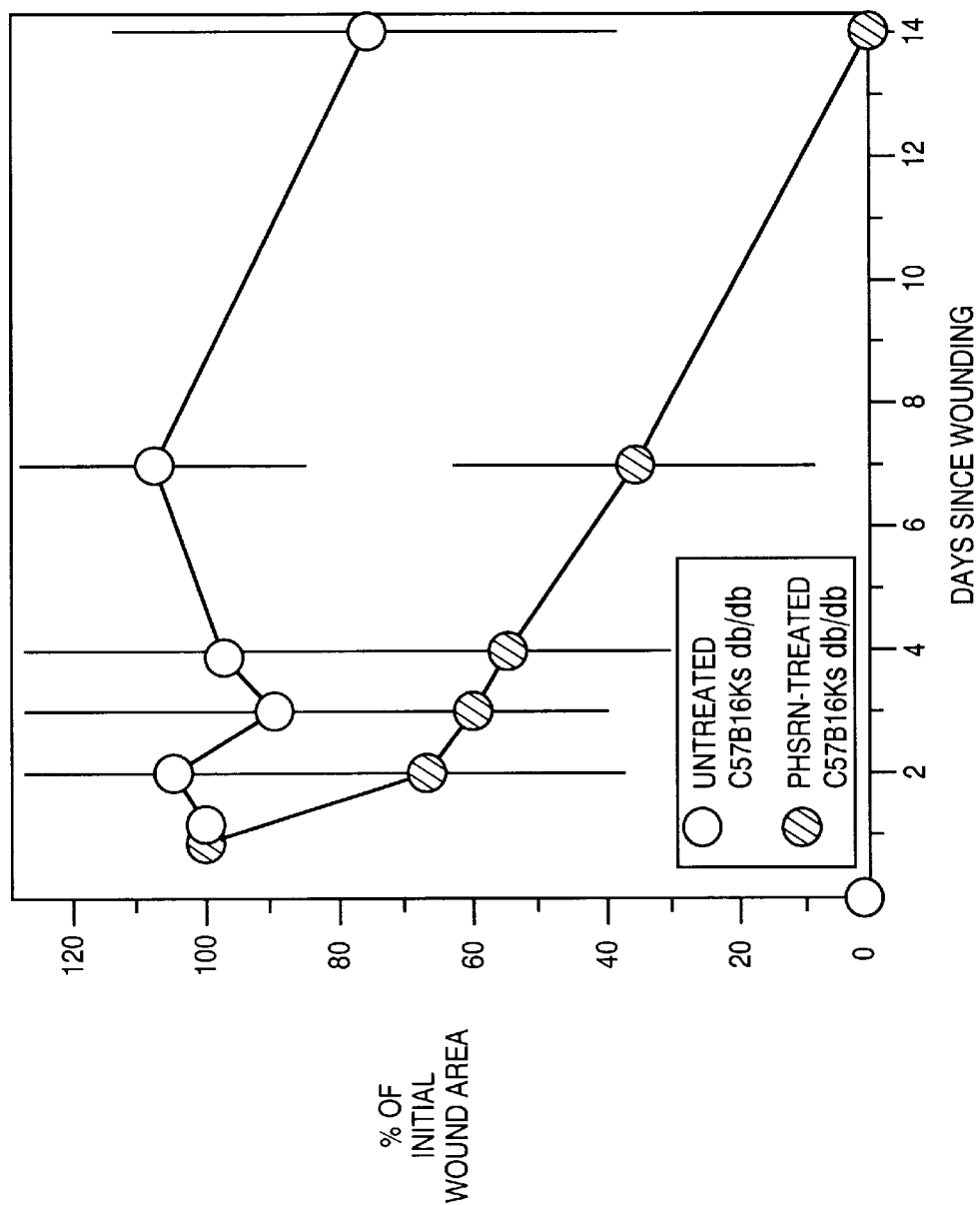
FIG. 8 is a graph presenting dermal wound closure data as a function of time in genetically obese/diabetic mice, and their controls, in response to treatment with peptides containing the amino acid sequence PHSRN (SEQ ID NO:1).

In this example, the effect of PHSRN (SEQ ID NO:1) on a dermal wound created on genetically obese, diabetic mice was considered. FIG. 8 presents the data from 10 mice wounded with 4 mm biopsy punch through skin on the back. Just after wounding, the 5 treated mice receive 5 microliters of normal saline containing 2 micrograms PHSRN (SEQ ID NO:1) peptide in their wounds. The 5 untreated mice received 5 microliters of normal saline without PHSRN (SEQ ID NO:1). Wound areas were measured on the days indicated by standard procedures in which a microscope slide is placed directly on the wound and its edges traced. The results show the rate of wound closure was accelerated in the PHRSN-treated (SEQ ID NO:1) group as compared to the untreated controls.

EXAMPLE 12

Comparative Wound Areas

In this example, the mean wound areas in PHSRN-treated (SEQ ID NO:1), and untreated normal and diabetic mice are considered. With respect to the diabetic mice, ten obese diabetic C57B16Ksdb/db mice received dermal wounds with a biopsy punch on day 0 according to standard methods. The wounds of 5 of these mice received 2 ug of the PHSRN (SEQ ID NO:1) peptide in 5μl normal saline without peptide. On the days indicated, the edges of all wounds were traced onto glass slides and the areas of the tracings determined in square mm. This is a standard method for wound area measurement in these mice. Six tracings of every wound were done on each day shown, and the mean wound areas determined.

With respect to non-diabetic littermates, eight non-diabetic C57B16Ks db/+ mice received duplicate dermal wounds with a biopsy punch on day 0 according to standard methods. 4 to 8 mm of unwounded skin separated each pair of wounds. One wound on each mouse received the PHSRN (SEQ ID NO:1) peptide as described above for the diabetic mice. The other wound received normal saline. On the days indicated, the edges of all wounds were traced onto glass slides for areas determination.

Figure 9:
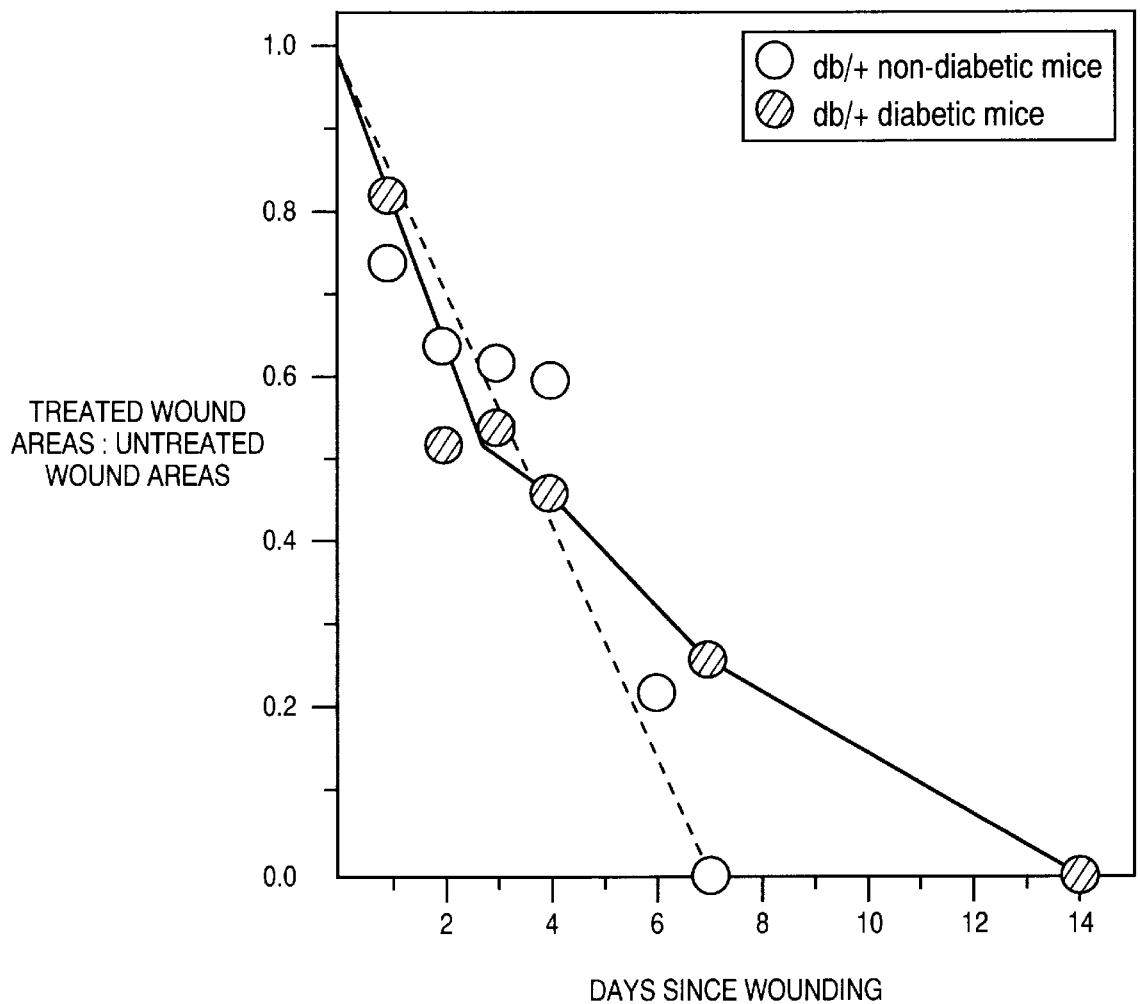
FIG. 9 is a graph presenting dermal wound closure data as a function of time in diabetic and non-diabetic mice treated with peptides containing the amino acid sequence PHSRN (SEQ ID NO:1).

As shown in FIG. 9, diabetic (db/db) and normal (db/+) mice both present ratios which fall to zero. This means the treated wounds all closed prior to the untreated ones. If the PHSRN (SEQ ID NO:1) had no effect, the ratios of the wound areas should remain at about 1. In the alternative, if the PHSRN (SEQ ID NO:1) peptide slowed wound healing with respect to untreated mice, the ratios should rise to infinity. Thus, a single application of the PHSRN (SEQ ID NO:1) peptide to the wound shortly after wounding dramatically stimulated wound healing in both normal and diabetic mice.

It should also be noted that the rate of wound healing in the treated cohort of mice, relative to the untreated cohort, is promoted approximately equally in normal and diabetic mice through day four. This interval corresponds to the time of provisional matrix induction (which requires invasion by fibroblasts, Leukocytes, and blood vessels). It should be noted from these data that in the later stages of wound healing (after the first 4 days) the diabetic mice are less responsive than the normal mice. These data are consistent with the hypothesis that other late-occurring processes, which are PHSRN-independent, (SEQ ID NO:1) may still occur more slowly in diabetic mice as compared to their normal littermates.

Figure 10:
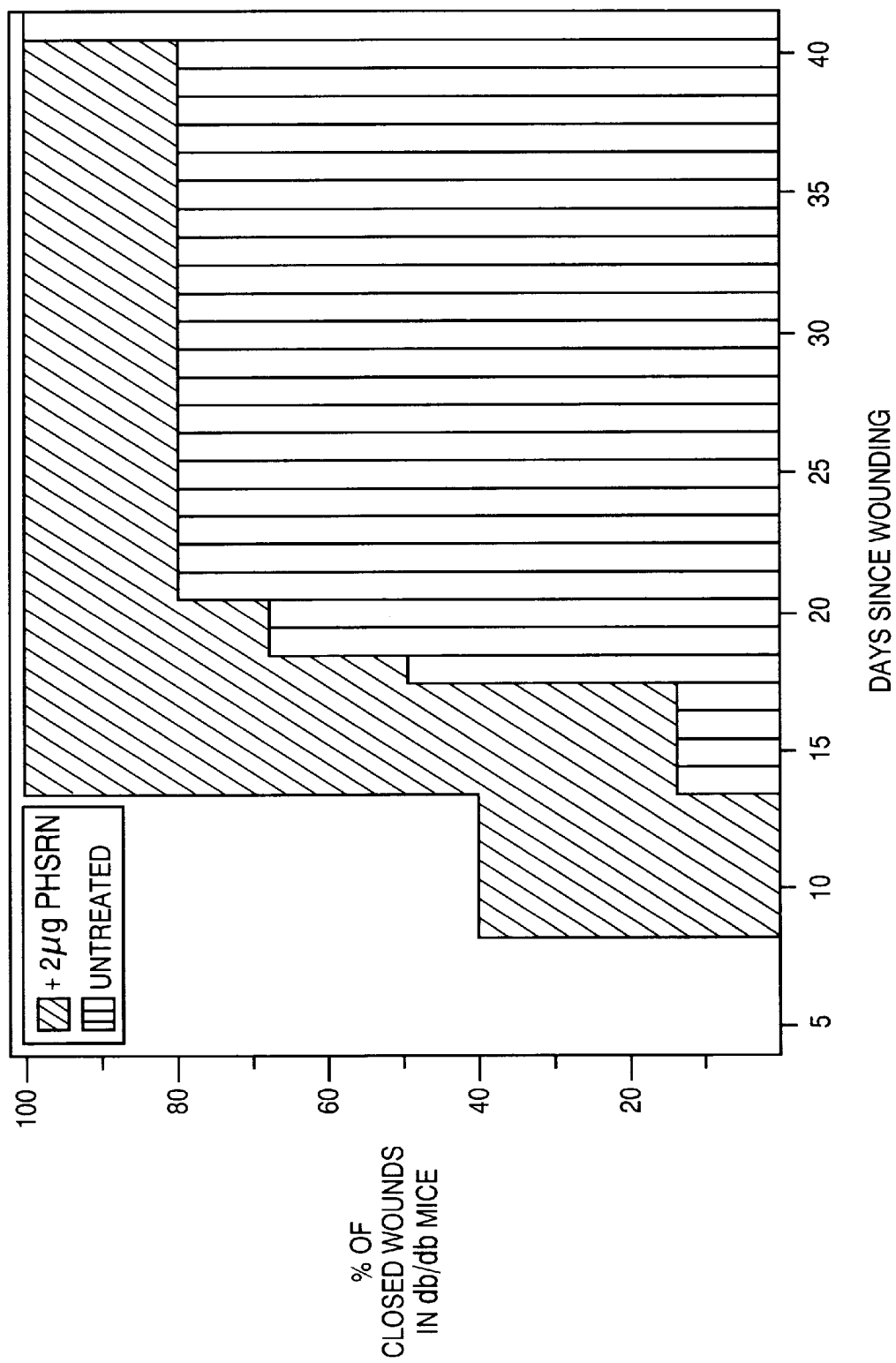
FIG. 10 is a graph presenting the percentages of closed wounds as a function of time in diabetic mice treated with peptides containing the amino acid sequence PHSRN (SEQ ID NO:1).

Expanding upon the data presented in FIG. 9, FIG. 10 presents the percentages of completely closed wounds in PHSRN-treated (SEQ ID NO:1) and untreated diabetic mice during the 41 day period after wounding by the above described wounding methods. Again, the results show that a single application of the PHSRN (SEQ ID NO:1) peptide to the wound shortly after wounding stimulated wound healing in both normal and diabetic mice.

From the above, it should be evident that the present invention provides methods and compositions for enhancing and promoting wound healing. Invasion-inducing agents can be readily identified using the assays described above. Thereafter, such agents can be modified or derivatized and used therapeutically by application directly on wounds.

I claim:

1. A peptide, comprising the amino acid sequence PHSRN (SEQ ID NO:1), wherein said peptide is protease resistant and comprises protecting groups.

2. The peptide of claim 1, wherein said peptide is N-terminally acetylated and C-terminally amidated.

3. The peptide of claim 2, wherein said peptide has the general formula:

Ac-XPHSRNX-NH$_2$(SEQ ID NO:84)

wherein Ac represents the acetylated N-terminus and X represents additional amino acids of between 0 and 100.

4. The peptide of claim 1, wherein said peptide comprises at least one D-amino acid.

5. The peptide of claim 1, wherein said peptide is immobilized on a solid support.

6. The peptide of claim 5, wherein said solid support comprises a dressing.

7. The peptide of claim 6, wherein said solid support comprises an adsorbent material.

8. The peptide of claim 7, wherein said adsorbent material is attached to an adhesive strip.

9. A peptide having the general formula

Ac-XPHSRNX-NH$_2$(SEQ ID NO:84)

wherein Ac represents the acetylated N-terminus and X represents additional amino acids of between 0 and 100.

10. The peptide of claim 9, wherein said peptide is immobilized on a solid support.

11. The peptide of claim 10, wherein said solid support comprises a dressing.

12. The peptide of claim 10, wherein said solid support comprises an adsorbent material.

13. The peptide of claim 12, wherein said adsorbent material is attached to an adhesive strip.

14. A peptide, comprising the amino acid sequence PHSRN (SEQ ID NO: 1), wherein said peptide comprises at least one D-amino acid.

15. The peptide of claim 14, wherein said peptide is immobilized on a solid support.

16. The peptide of claim 15, wherein said solid support comprises a dressing.

17. The peptide of claim 15, wherein said solid support comprises an adsorbent material.

18. The peptide of claim 17, wherein said adsorbent material is attached to an adhesive strip.

* * * * *